(12) United States Patent
Noch et al.

(10) Patent No.: US 12,127,844 B2
(45) Date of Patent: *Oct. 29, 2024

(54) METHOD AND APPARATUS FOR MOBILE STROKE SELF-DETECTION

(71) Applicant: Destroke, Inc., Brooklyn, NY (US)

(72) Inventors: Evan Noch, New York, NY (US); Tomer M. Yaron, New York, NY (US); Ciarra King, New York, NY (US); Dmitrii Meleshko, New York, NY (US); Yubin Xie, New York, NY (US); Suniyya Waraich, New York, NY (US); James Hess, Wesley Chapel, FL (US); Dan Pham, San Jose, CA (US)

(73) Assignee: Destroke, Inc., Brooklyn, NY (US)

( * ) Notice: Subject to any disclaimer, the term of this patent is extended or adjusted under 35 U.S.C. 154(b) by 183 days.

This patent is subject to a terminal disclaimer.

(21) Appl. No.: 17/962,600

(22) Filed: Oct. 10, 2022

(65) Prior Publication Data
US 2023/0030004 A1 Feb. 2, 2023

Related U.S. Application Data

(63) Continuation-in-part of application No. 16/861,363, filed on Apr. 29, 2020, now Pat. No. 11,468,995.

(60) Provisional application No. 62/842,952, filed on May 3, 2019.

(51) Int. Cl.
| | | |
|---|---|---|
| *G06T 7/70* | (2017.01) | |
| *A61B 5/00* | (2006.01) | |
| *G06T 7/20* | (2017.01) | |
| *G10L 15/26* | (2006.01) | |

(52) U.S. Cl.
CPC ........... *A61B 5/4064* (2013.01); *A61B 5/746* (2013.01); *G06T 7/20* (2013.01); *G06T 7/70* (2017.01); *G10L 15/26* (2013.01); *A61B 2562/0219* (2013.01); *G06T 2207/30041* (2013.01); *G06T 2207/30201* (2013.01)

(58) Field of Classification Search
CPC ................. A61B 5/4064; A61B 5/746; A61B 2562/0219; G06T 7/70; G06T 7/20; G06T 2207/30041; G06T 2207/30201; G10L 15/26
USPC ........................................ 345/661
See application file for complete search history.

(56) References Cited

U.S. PATENT DOCUMENTS

| | | | | |
|---|---|---|---|---|
| 2011/0106200 A1* | 5/2011 | Ziegler | ................. | A61B 5/7275 607/18 |
| 2013/0218588 A1* | 8/2013 | Kehr | ...................... | G16H 40/63 705/2 |
| 2018/0153477 A1* | 6/2018 | Nagale | ................... | A61B 5/021 |

(Continued)

*Primary Examiner* — Hai Tao Sun
(74) *Attorney, Agent, or Firm* — Young Basile Hanlon & MacFarlane, P.C.

(57) ABSTRACT

Disclosed herein are implementations of a method and apparatus for stroke self-detection. The method and apparatus may include a mobile platform for stroke detection. The method may include receiving sensor data. The method may include comparing the sensor data with a baseline test result to determine a test score. The method may include determining a passing test result based on a threshold. The method may include transmitting the results or an alert to one or more of an emergency contact, emergency medical services, a physician, or a telemedicine provider.

17 Claims, 15 Drawing Sheets

(56) References Cited

U.S. PATENT DOCUMENTS

| | | |
|---|---|---|
| 2018/0164610 A1 | 6/2018 | Liang |
| 2018/0249967 A1* | 9/2018 | Lederman .............. G16H 50/30 |
| 2019/0362707 A1 | 11/2019 | Meng et al. |
| 2021/0030299 A1* | 2/2021 | Naber .................. A61B 5/7267 |

* cited by examiner

METHOD AND APPARATUS FOR MOBILE STROKE SELF-DETECTION

CROSS-REFERENCE TO RELATED APPLICATION

This application is a continuation-in-part of U.S. patent application Ser. No. 16/861,363, filed Apr. 29, 2020, which claims priority to and the benefit of U.S. Provisional Patent Application No. 62/842,952, filed May 3, 2019, the entire disclosure of which is hereby incorporated by reference.

SUMMARY

Disclosed herein are implementations of a method and apparatus for stroke self-detection. The method and apparatus may include a mobile platform for stroke self-detection. The apparatus may be configured to receive sensor data. The apparatus may be configured to compare the sensor data with a baseline test result to determine a test score. The apparatus may be configured to determine a passing test result based on a threshold.

In an aspect, a computing device for stroke detection may include a display, a plurality of sensors, a memory, and a processor. The display may be configured to display an instruction. The plurality of sensors may include an accelerometer, a camera, and a microphone. The processor may be configured to obtain sensor data based on the instruction. The sensor data may include accelerometer data from the accelerometer, image capture data from the camera, and microphone data from the microphone. The microphone data may include voice data associated with a patient response. The processor may be configured to convert the voice data to text data. The processor may be configured to determine a stroke self-detection score based on the obtained sensor data. The determination of the stroke self-detection score may include a comparison of the text data to data associated with the instruction and a determination of a cognitive score. The instruction may include a request for patient age. The determination of the cognitive score may include a determination that the cognitive score is zero (0) on a condition that the text data matches the data associated with the instruction. The determination of the cognitive score may include a determination that the cognitive score is one (1) on a condition that the text data does not match the data associated with the instruction. The computing device may be configured to store the stroke self-detection score in the memory. The computing device may be configured to display the stroke self-detection score on the display as a result summary. The computing device may be configured to transmit an alert when the stroke self-detection score is above a threshold.

In an aspect, a computing device may include a display, a microphone, a memory, and a processor. The display may be configured to display an instruction. The processor may be configured to obtain microphone data from the microphone. The microphone data may include voice data associated with a patient response. The processor may be configured to convert the voice data to text data. The processor may be configured to determine a stroke self-detection score based on a comparison of the text data to data associated with the instruction and a determination of a cognitive score. The instruction may include a request for a current month. The determination of the cognitive score may include a determination that the cognitive score is zero (0) on a condition that the text data matches the data associated with the instruction. The determination of the cognitive score may include a determination that the cognitive score is one (1) on a condition that the text data does not match the data associated with the instruction. The computing device may be configured to store the stroke self-detection score in the memory. The computing device may be configured to display the stroke self-detection score on the display as a result summary. The computing device may be configured to transmit an alert if the stroke self-detection score is above a threshold.

In an aspect, a method for stroke self-detection may include displaying an instruction on a display. The method may include obtaining sensor data. The sensor data may be based on the instruction. The sensor data may include accelerometer data, image capture data, microphone data, or any combination thereof. The method may include determining a stroke self-detection score. The stroke self-detection score may be based on the obtained sensor data. The method may include storing the stroke self-detection score in a memory. The method may include displaying the stroke self-detection score on the display as a result summary. The method may include transmitting an alert if the stroke self-detection score is above a threshold.

In an aspect, a method for stroke self-detection may include displaying an instruction on a display. The method may include obtaining sensor data based on the instruction. The sensor data may include microphone data. The microphone data may include voice data associated with a patient response. The method may include converting the voice data to text data. The method may include determining a stroke self-detection score by comparing the text data to data associated with the instruction. The method may include storing the stroke self-detection score in a memory. The method may include displaying the stroke self-detection score on the display as a result summary. The method may include transmitting an alert if the stroke self-detection score is above a threshold.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

DETAILED DESCRIPTION

Figure 1:
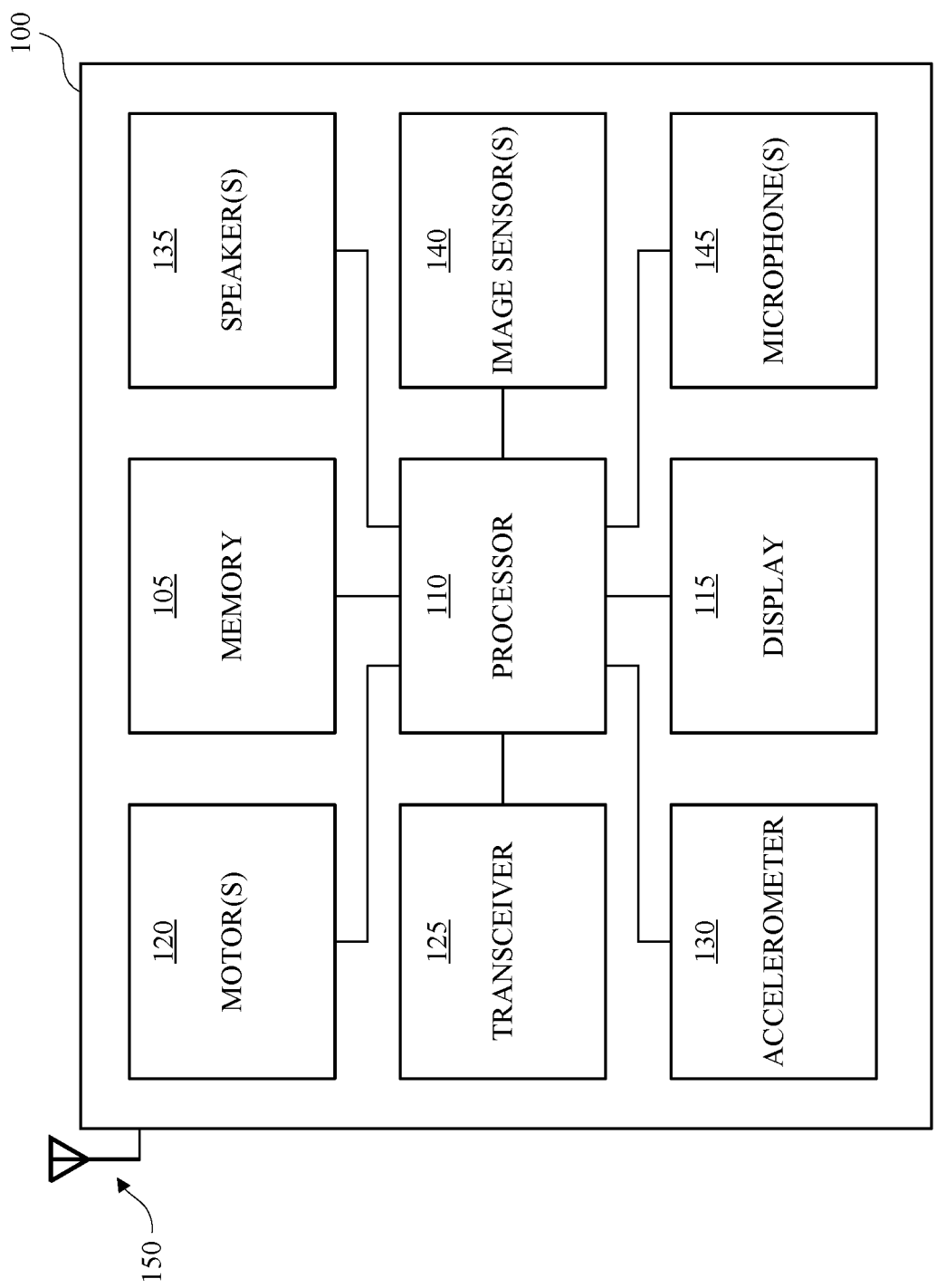
FIG. 1 is a diagram of an example of a computing device in accordance with implementations of this disclosure.

Over 800,000 strokes occur yearly, and are the leading cause of disability in the United States. Patients lose two million neurons per second during a stroke. 20-25% of patients get help within 3 hours. Typical stroke detection methods require a physician, and the majority of patients do not make it to the hospital soon enough to receive adequate treatment. Accordingly, it would be desirable to have a method and apparatus for a patient to self-detect a stroke without the need of a physician being present.

The systems and methods described herein may be used by a patient to self-detect a stroke without the need of a physician being present. The stroke self-detection systems and methods may be based on the National Institute of Health stroke scale.

As used herein, the terminology "computer" or "computing device" includes any unit, or combination of units, capable of performing any method, or any portion or portions thereof, disclosed herein.

As used herein, the terminology "processor" indicates one or more processors, such as one or more special purpose processors, one or more digital signal processors, one or more microprocessors, one or more controllers, one or more microcontrollers, one or more application processors, one or more central processing units (CPU)s, one or more graphics processing units (GPU)s, one or more digital signal processors (DSP)s, one or more application specific integrated circuits (ASIC)s, one or more application specific standard products, one or more field programmable gate arrays, any other type or combination of integrated circuits, one or more state machines, cloud-based computing processors, or any combination thereof.

As used herein, the terminology "memory" indicates any non-transitory computer-usable or computer-readable medium or device that can tangibly contain, store, communicate, or transport any signal or information that may be used by or in connection with any processor. For example, a memory may be one or more read only memories (ROM), one or more random access memories (RAM), one or more registers, low power double data rate (LPDDR) memories, one or more cache memories, one or more semiconductor memory devices, one or more magnetic media, one or more optical media, one or more magneto-optical media, or any combination thereof.

As used herein, the terminology "instructions" may include directions or expressions for performing any method, or any portion or portions thereof, disclosed herein, and may be realized in hardware, software, cloud-based computing environment(s), or any combination thereof. For example, instructions may be implemented as information, such as a computer program, stored in memory that may be executed by a processor to perform any of the respective methods, algorithms, aspects, or combinations thereof, as described herein. Instructions, or a portion thereof, may be implemented as a special purpose processor, or circuitry, that may include specialized hardware for carrying out any of the methods, algorithms, aspects, or combinations thereof, as described herein. In some implementations, portions of the instructions may be distributed across multiple processors on a single device, on multiple devices, which may communicate directly or across a network such as a local area network, a wide area network, the Internet, or a combination thereof.

As used herein, the terminology "determine" and "identify," or any variations thereof, includes selecting, ascertaining, computing, looking up, receiving, determining, establishing, obtaining, or otherwise identifying or determining in any manner whatsoever using one or more of the devices and methods shown and described herein.

As used herein, the terminology "example," "embodiment," "implementation," "aspect," "feature," or "element" indicates serving as an example, instance, or illustration. Unless expressly indicated, any example, embodiment, implementation, aspect, feature, or element is independent of each other example, embodiment, implementation, aspect, feature, or element and may be used in combination with any other example, embodiment, implementation, aspect, feature, or element.

As used herein, the terminology "or" is intended to mean an inclusive "or" rather than an exclusive "or." That is, unless specified otherwise, or clear from context, "X includes A or B" is intended to indicate any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from the context to be directed to a singular form.

Further, for simplicity of explanation, although the figures and descriptions herein may include sequences or series of steps or stages, elements of the methods disclosed herein may occur in various orders or concurrently. Additionally, elements of the methods disclosed herein may occur with other elements not explicitly presented and described herein. Furthermore, not all elements of the methods described herein may be required to implement a method in accordance with this disclosure. Although aspects, features, and elements are described herein in particular combinations, each aspect, feature, or element may be used independently or in various combinations with or without other aspects, features, and elements.

One or more embodiments disclosed herein may include an example of a platform configured to allow a patient to self-detect a stroke. The platform may be implemented on any computing device, for example, a mobile device such as a mobile telephone, a tablet, or a wearable device. The platform includes a user interface. The user interface may include a touch display. The platform may obtain information via the user interface. The information may include patient information, including, for example, patient name, address, age, height, weight, and gender. The information may include an emergency contact name, contact number, physician name, physician number, or any combination thereof. The information may include past medical history, medication, or both.

The platform may be configured to perform one or more tests via the user interface. One or more tests may use facial recognition, speech analysis, object recognition, motion recognition, or any combination thereof. The one or more tests may use one or more sensors of the mobile device, including, for example, a camera, depth sensor, accelerometer, gyroscope, a global positioning system (GPS), microphone, or any combination thereof. For example, the camera, depth sensor, or both, may be used to obtain a point cloud from one or more images to determine a face for facial recognition. In another example, the camera may be used either alone or in conjunction with the accelerometer to determine motion. The one or more tests may include a baseline test. The baseline test may be performed any number of times to determine a baseline for each patient. Any subsequent test result may be compared with the baseline test result to determine whether the patient is experiencing a stroke. In some implementations, the platform may be configured to automatically contact the patient's physician if it is determined that the patient is experiencing a stroke. Patient data may be stored on the device, on a cloud server, or both. The patient data may include patient profile data and test data. The patient profile data may include the patient's name, medical history, medications, allergies, emergency contact information, physician contact information, or any combination thereof.

An example of voice recognition may include obtaining voice samples from the patient of known words or phrases and comparing the obtained voice samples with the patient's baseline test result. The system may determine a score based on the baseline test result. For example, a score close to 1 may be normal, and a score close to 0 may be indicative of a complete mismatch, i.e. a high risk for a stroke.

The platform may be configured to generate displays of test results. For example, a pass indication and a fail indication for each test conducted may be displayed on the user interface. Any indication may be used to show pass or fail. For example, the pass indication may be shown as a check mark, and the fail indication may be shown as an "X." In some examples, the test results may trigger the summary display. If the number of abnormal test results is above a threshold, the platform may automatically contact the patient's physician, emergency services, one or more of the patient's emergency contacts, or any combination thereof. The threshold may be any value that is above a patient's baseline.

FIG. 1 is a diagram of an example of a computing device 100 that may be used to implement any of the systems and platforms described herein. The computing device 100 may be a hardware device, or it may be implemented in software as a virtual machine. The computing device 100 may include a smartphone, tablet, wearable device, or personal computing device. The computing device 100 includes a memory 105, a processor 110, a display 115, one or more motors 120, a transceiver 125, an accelerometer 130, one or more speakers 135, one or more image sensors 140, one or more microphones 145, one or more antennas 150, or any combination thereof. For example, some implementations of the computing device 100 may not include the display 115.

The memory 105 may include a system memory module that is configured to store executable computer instructions that, when executed by processor, control various functions of the computing device. The memory may include non-transitory memory configured to store patient data, self-detection request data, self-detection response data, or any combination thereof. Patient data may include patient medical history data, emergency contact information, physician contact information, patient address data, patient medical insurance data, or any combination thereof. Self-detection request data may include request data to solicit patient input for self-detection purposes. The self-detection request data may include text data, text-to-speech data, or both. Self-detection response data may include patient voice data obtained in response to the self-detection request. The self-detection response data may include speech-to-text data, voice data, or both.

The processor 110 may include a system on a chip (SOC) microcontroller, microprocessor, CPU, DSP, ASIC, GPU, or other processors that control the operation and functionality of the computing device. The processor 110 may interface with mechanical, electrical, sensory, and power modules via driver interfaces and software abstraction layers. Additional processing and memory capacity may be used to support these processes. These components may be fully controlled by the processor 110. In some implementations, one or more components may be operable by one or more other control processes in accordance with a given schedule. The memory 105 may include a database that is configured to store information from the processor 110. The processor 110 may be configured to receive an electrical signal associated with an audible sound (e.g., a voice input) from the one or more microphones 145, and convert the audible sound to text. The processor 110 may be configured to obtain a text instruction, convert the text instruction to a speech signal, and transmit the speech signal to the one or more speakers 135.

The display 115 may include an interactive touch display. The display 115 may be a liquid crystal display (LCD) display unit, a light-emitting diode (LED) display unit, an organic light-emitting diode (OLED) display unit, or a micro organic light-emitting diode (micro-OLED) display unit. The display 115 may be a capacitive display that is configured to receive a user input, for example, via a touch or gesture.

The one or more motors 120 may include an eccentric rotating motor (ERM), a linear resonant actuator (LRA), or both. The one or more motors 120 are configured to vibrate to provide haptic feedback. The one or more motors 120 may collectively be referred to as a haptic engine or a taptic engine. The one or more motors 120 may receive a signal from the processor 110 causing the one or more motors 120 to vibrate. The signal received from the processor 110 may be a control signal. The control signal may be received via one or more haptic drivers. In an example, the control signal from the processor 110 may cause the one or more haptic drivers to transmit a current to the one or more motors 120. The current may be modulated to vary the strength of the vibrations generated by the one or more motors 120.

The transceiver 125 is coupled to the processor 110 and the one or more antennas 150. Although the transceiver 125 is shown as a single unit, some embodiments may implement the transceiver 125 as a separate receiver unit and transmitter unit. While FIG. 1 depicts the processor 110 and the transceiver 125 as separate components, it will be appreciated that the processor 110 and the transceiver 125 may be integrated together in an electronic package or chip. The transceiver 125 may be configured to modulate signals that are to be transmitted by the one or more antennas 150 and to demodulate the signals that are received by the one or more antennas 150. The transceiver 125 may include multiple transceivers for enabling the computing device 100 to communicate via multiple radio access technologies.

The accelerometer 130 may be a single-axis or multi-axis component that is configured to detect magnitude and direction of the proper acceleration as a vector quantity. The magnitude and direction of the proper acceleration may be used to sense orientation, coordinate acceleration, vibration, shock, and falling in a resistive medium. For example, the accelerometer 130 may be configured to detect whether an extended arm of a patient is shaking or drifting in a downward or sideways direction and generate and transmit a signal to the processor 110. The processor 110 may be configured to determine whether an extended arm of a patient is shaking or drifting in a downward or sideways direction based on the accelerometer signal. In some implementations, the accelerometer 130 may be a micromachined microelectromechanical system (MEMS) accelerometer configured to detect the position of the computing device 100 and provide input for stroke self-detection and determination.

The one or more speakers 135 may each be an electroacoustic transducer configured to convert an electrical audio signal from the processor 110 into a corresponding sound in the audible frequency range (e.g., about 20 Hz to about 20 KHz). In one or more embodiments, the one or more speakers 135 may be configured to transmit sound in the form of a voice request to illicit a user response.

The one or more image sensors 140 are configured to detect and convey information used to make an image. The one or more image sensors 140 may be configured to convert the variable attenuation of light waves into signals that convey the information. The waves may be light or other electromagnetic radiation. The one or more image sensors 140 may include digital cameras, depth sensors, infrared (IR) sensors, or any combination thereof. The one or more image sensors 140 may be configured to capture images, video, or both.

The one or more microphones 145 may each be a transducer configured to convert an audible sound into an electrical signal. The one or more microphones 145 may include a dynamic microphone, a condenser microphone, a piezoelectric microphone, or any combination thereof.

The one or more antennas 150 may be configured to transmit signals to, or receive signals from, a wireless device, such as a base station, over an air interface. For example, in one embodiment, the one or more antennas 150 may be configured to transmit and/or receive radio frequency (RF) signals. In another embodiment, the one or more antennas 150 may be an emitter/detector configured to transmit and/or receive IR, ultraviolet (UV), or visible light signals, for example. In yet another embodiment, the one or more antennas 150 may be configured to transmit and receive both RF and light signals. It will be appreciated that the one or more antennas 150 may be configured to transmit and/or receive any combination of wireless signals.

Figure 2:
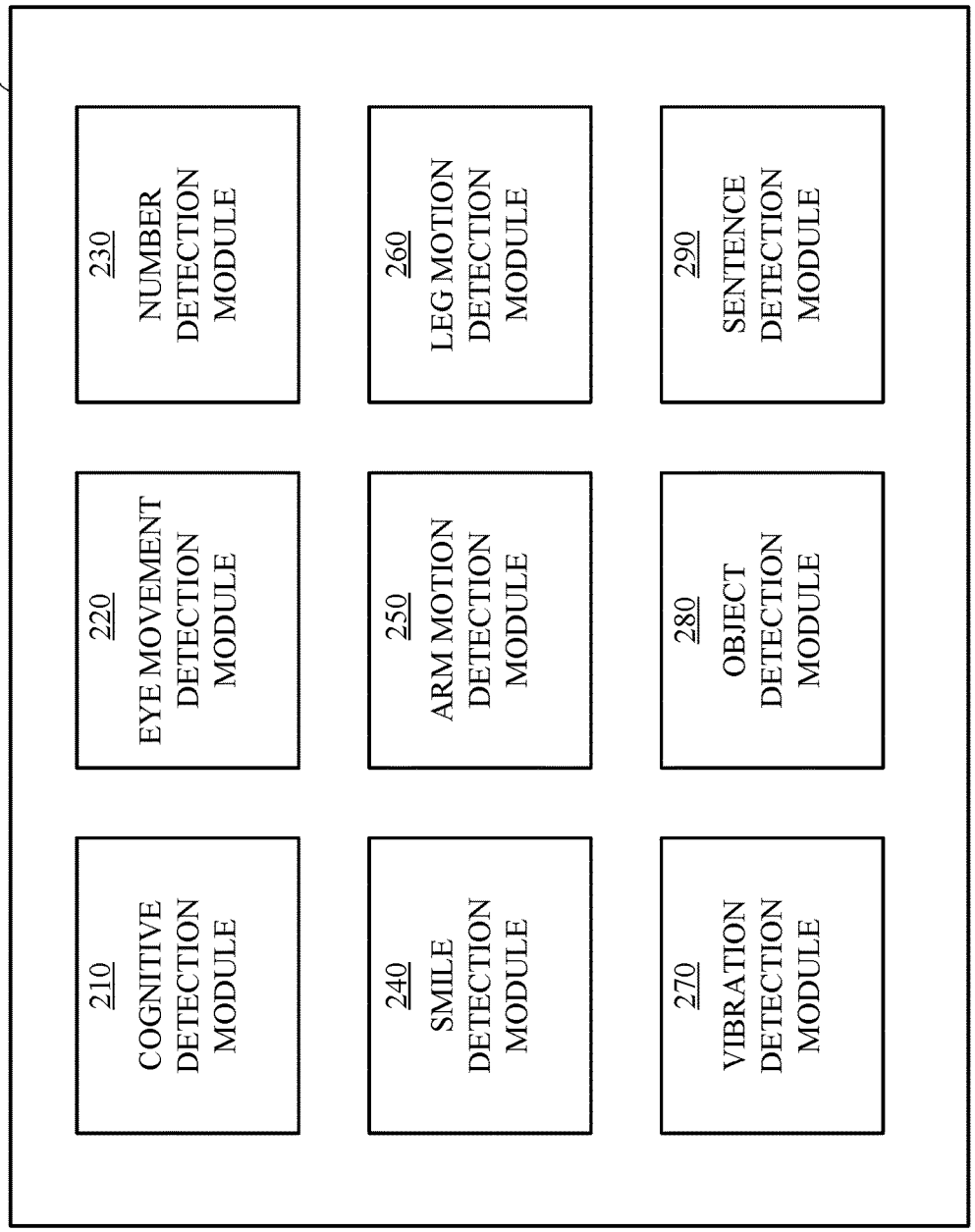
FIG. 2 is a diagram of an example of the processor shown in FIG. 1 in accordance with implementations of this disclosure.

FIG. 2 is a block diagram of an example of the processor 110 shown in FIG. 1. As shown in FIG. 2, the processor 110 includes a cognitive detection module 210, an eye movement detection module 220, a number detection module 230, a smile detection module 240, an arm motion detection module 250, a leg motion detection module 260, a vibration detection module 270, an object detection module 280, and a sentence detection module 290. The processor 110 may be configured to execute instructions from a non-transitory computer readable medium based on the cognitive detection module 210, the eye movement detection module 220, the number detection module 230, the smile detection module 240, the arm motion detection module 250, the leg motion detection module 260, the vibration detection module 270, the object detection module 280, the sentence detection module 290, or any combination thereof. Each module shown in FIG. 2 is configured to determine one or more respective stroke self-detection scores. One or more of the determined stroke self-detection scores may be summed to determine an overall score.

Figure 3:
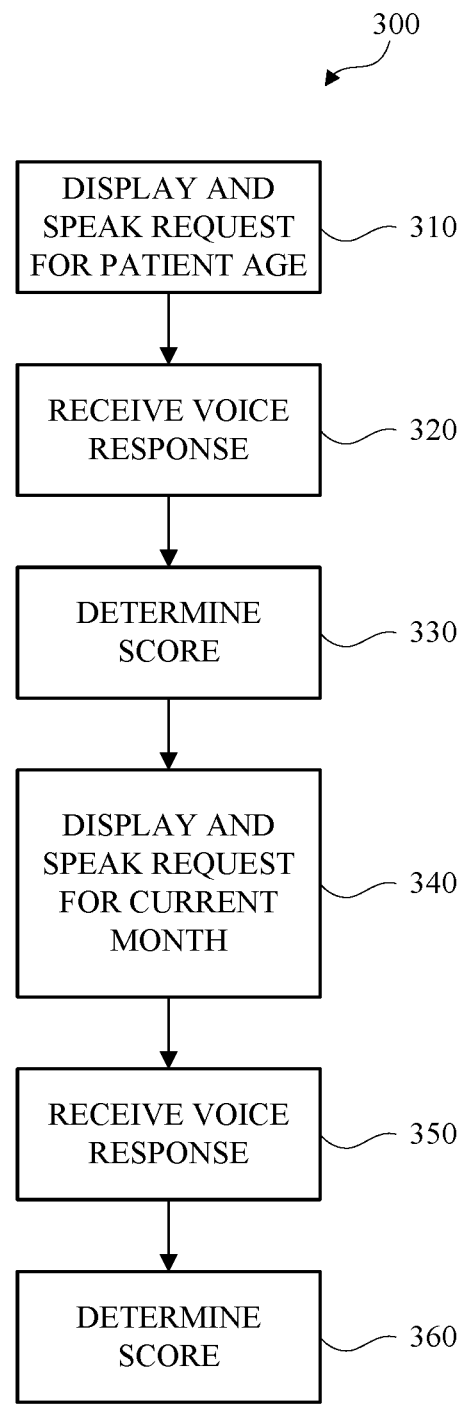
FIG. 3 is a flow diagram of an example of a method for stroke self-detection in accordance with embodiments of this disclosure.

FIG. 3 is a flow diagram of an example of a method 300 for stroke self-detection in accordance with embodiments of this disclosure. The method 300 may be performed by the processor 110 shown in FIGS. 1 and 2. In this example, the method 300 may be performed by the cognitive detection module 210 shown in FIG. 2.

As shown in FIG. 3, the method 300 includes displaying and speaking 310 a request for patient age. For example, the cognitive detection module 210 may cause the processor 110 to send a signal to the display 115 shown in FIG. 1 to display text of the request for patient age, send a signal to the one or more speakers 135 shown in FIG. 1 to speak the request for patient age, or both. In an example, the text "How old are you?" may be displayed on the display 115 and the audible phrase "How old are you?" may be emitted from the one or more speakers 135.

The method 300 includes receiving 320 a voice response. The voice response may be received by the one or more microphones 145 shown in FIG. 1. The voice response may be processed using any open source speech recognition technique. The voice response may be received as an audible phrase such as, for example, "forty-five," "forty-five years," or "I am forty-five years old." The one or more microphones 145 may be configured to transmit a signal associated with the voice response to the processor 110. The cognitive determination module 210 may cause the processor to convert the received signal associated with the voice response to text and compare the text to age data in a user profile.

The method 300 includes determining 330 a score, for example, a stroke self-detection score. The score may be referred to as a cognitive score or a cognition detection score. The score may be based on a determination of whether the text associated with the voice response matches the age data in the user profile. If the text associated with the voice response matches the age data in the user profile, a determination is made that the response was correct, and a score of zero (0) is determined. If the text associated with the voice response does not match the age data in the user profile, a determination is made that the response was incorrect, and a score of one (1) is determined. The score may be stored, for example in memory 105 shown in FIG. 1, for later calculation and tabulation.

The method 300 includes displaying and speaking 340 a request for the current month. For example, the cognitive detection module 210 may cause the processor 110 to send a signal to the display 115 shown in FIG. 1 to display text of the request for the current month, send a signal to the one or more speakers 135 shown in FIG. 1 to speak the request for the current month, or both. In an example, the text "What month is it?" may be displayed on the display 115 and the audible phrase "What month is it?" may be emitted from the one or more speakers 135.

The method 300 includes receiving 350 a voice response. The voice response may be received by the one or more microphones 145 shown in FIG. 1. The voice response may be received as an audible phrase such as, for example, "April" or "It is April." The one or more microphones 145 may be configured to transmit a signal associated with the voice response to the processor 110. The cognitive determination module 210 may cause the processor to convert the received signal associated with the voice response to text and compare the text to the current date, for example, in a calendar module.

The method 300 includes determining 360 a score, for example, a stroke self-detection score. The score may be referred to as a cognitive score or a cognition detection score. The score may be based on a determination of whether the text associated with the voice response matches the current date. If the text associated with the voice response matches the current date, a determination is made that the response was correct, and a score of zero (0) is determined. If the text associated with the voice response does not match the current date, a determination is made that the response was incorrect, and a score of one (1) is determined. The score may be stored, for example in memory 105 shown in FIG. 1, for later calculation and tabulation.

Figure 4:
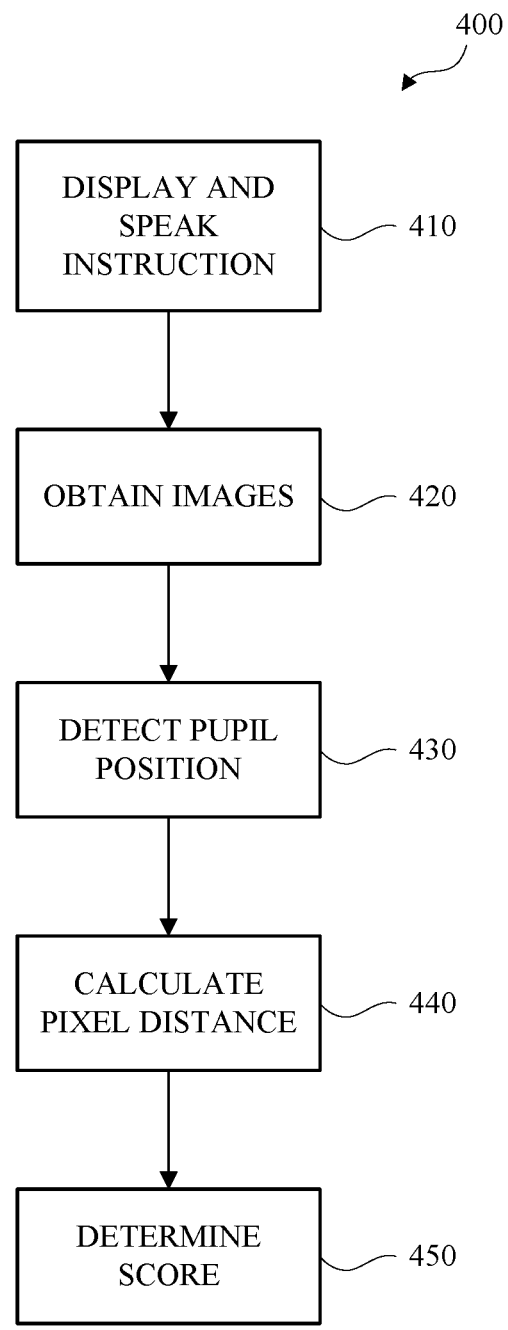
FIG. 4 is a flow diagram of another example of a method for stroke self-detection in accordance with embodiments of this disclosure.

FIG. 4 is a flow diagram of another example of a method 400 for stroke self-detection in accordance with embodiments of this disclosure. The method 400 may be performed by the processor 110 shown in FIGS. 1 and 2. In this example, the method 400 may be performed by the eye movement detection module 220 shown in FIG. 2.

As shown in FIG. 4, the method 400 includes displaying and speaking 410 an instruction. For example, the eye movement detection module 220 may cause the processor 110 to send a signal to the display 115 shown in FIG. 1 to display text of the instruction, send a signal to the one or more speakers 135 shown in FIG. 1 to speak the instruction, or both. In an example, the text "Keep your head still. With your eyes only, look to the left and look to the right." may be displayed on the display 115 and the audible phrase "Keep your head still. With your eyes only, look to the left and look to the right." may be emitted from the one or more speakers 135.

The eye movement detection module 220 may cause the processor 110 to send a signal to the one or more image sensors 140 shown in FIG. 1 to initiate a video recording of the face of the patient. In some implementations, the video recording may be stored in the memory 105 shown in FIG. 1. The processor 110 may obtain images 420 from the video recording. The processor 110 may perform face and face landmark detection, text detection, image registration, and general feature tracking using any open source technique. The processor 110 may use machine learning (ML) models for tasks such as classification or object detection using any open source technique. The processor 110 may be configured to track multiple objects, such as a patient's pupils, or rectangles throughout the video recording.

The processor 110 may identify and segment objects of the patient's face, for example, eyes, eyebrows, mouth, nose, or any combination thereof. Once the eyes are detected and segmented, the processor 110 may detect 430 pupil position. In an example, the iris and the pupil may be detected as one object. The processor 110 may detect the pupil position in one or more frames of the video recording. For each frame that the pupil position is detected, the processor 110 calculates 440 a pixel distance from the outer edge of the pupil to the corner of the eye in the direction of the eye movement (i.e., the left corner of the left eye or the right corner of the right eye). An indication that the patient is able to move their eyes to each side may be that the respective pupil is close to the edge of the respective eye.

The eye movement detection module 220 may cause the processor 110 to determine 450 a score, for example, a stroke self-detection score, based on the calculated pixel distance. The score may be referred to as an eye movement score or an eye movement detection score. The score may be based on the frame that has the smallest pixel distance. In an example, the processor 110 may determine a score of zero (0) if the pixel distance is less than 2 pixels. If the pixel distance is greater than 2 pixels when the patient looks to either the left side or the right side, the processor may determine a score of one (1). If the pixel distance is greater than 2 pixels when the patient looks to the left side and the right side, the processor 110 may determine a score of two (2). Forced deviation of eyes to one side may also result in the processor 110 determining a score of two (2). In an example of forced deviation, if the pixel distance is less than 2 pixels when the patient looks to either the left side or the right side and, simultaneously, the pixel distance of the opposite side is greater than 15 pixels, the processor 110 may determine a score of two (2). The score may be stored, for example in memory 105 shown in FIG. 1, for later calculation and tabulation.

In another example, the total score for eye movements may be determined by individual scores for each eye. The processor 110 may record the smallest distance between the left pupil and the leftmost corner of the left eye. Similarly, the processor 110 may record the smallest distance between the right pupil and the rightmost corner of the right eye. In this example, an example passing score may be 0.07 for the left eye, and 0.1 for the right eye. The scores are based on the relative positioning of the pupil inside a 1.0×1.0 bounding box that an eye tracking computer vision algorithm places around the eye. For the eyes, there are no units of measurement. Software running on the processor 110 can be used to detect the patient's facial feature (i.e., eye) and places a bounding box around the feature. The software normalizes the coordinates to the dimensions of the bounding box. For the eyes, the processor 110 records the x data points, which track where the pupil is located in relation to the bounding box surrounding the eye. The origin (0.0, 0.0) is at the lower-left corner of the bounding box, and the upper-right corner of the bounding box is (1.0, 1.0), similar to an (x, y) coordinate system.

If either the smallest left eye distance is greater than the passing score or the smallest right eye distance is greater than the passing score, then the patient receives a total score of one (1). If both the smallest left eye distance is greater than the passing score and the smallest right eye distance is greater than the passing score, then the patient receives a total score of two (2). If one eye receives a passing score and the other eye receives a failing score, then the patient receives a total score of two (2). If the patient receives a passing score on both eyes, then the patient receives a total score of zero (0).

Figure 5A:
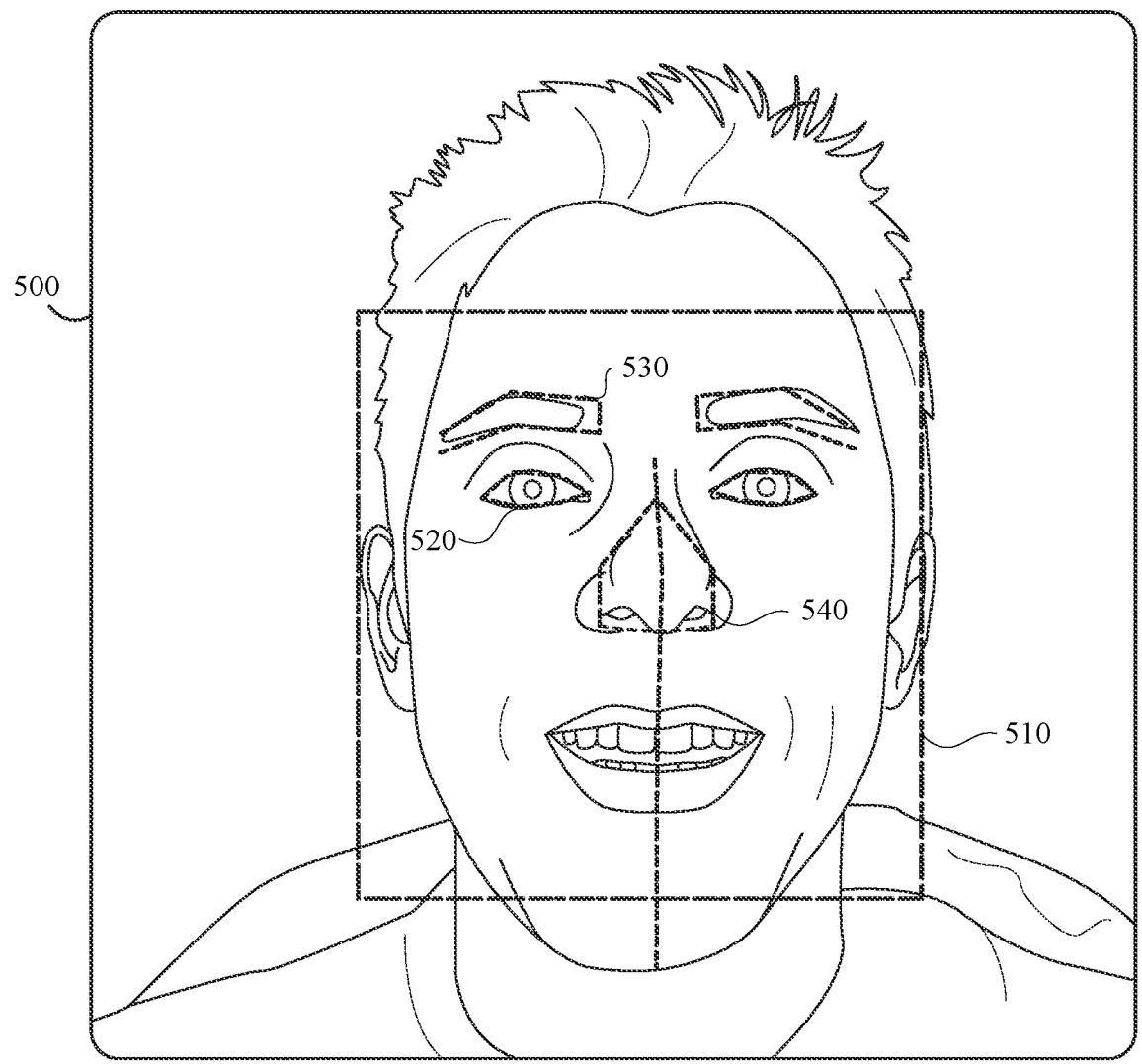
FIG. 5A is a diagram of an example of an image for face detection.

FIG. 5A is a diagram of an example of an image 500 for face detection. Detecting objects of the patient's face may include detecting all detectable two-dimensional (2D) face landmarks and regions, and exposing the face landmarks and regions as properties. As shown in FIG. 5A, the coordinates of the face landmarks may be normalized to the dimensions of a face bounding box 510, with the origin at the bounding box's lower-left corner. An image point function may be used to convert normalized face landmark points into absolute points within the coordinate system of the image or frame. As shown in FIG. 5A, detected objects (shown in bounding boxes as dashed lines) of the patient's face may include, for example, eyes 520, eyebrows 530, and nose 540.

Figure 5B:
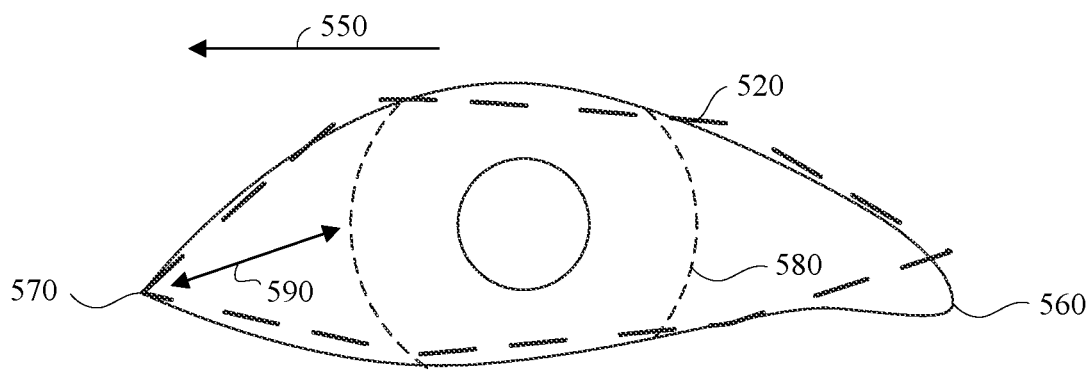
FIG. 5B is a diagram of the image shown in FIG. 5A enlarged to show pixel distance based on pupil position.

FIG. 5B is a diagram of the image 500 enlarged to show pixel distance based on pupil position. In this example, the patient's right eye is shown. The direction of eye movement is shown with arrow 550 when the patient looks to the right. As shown in FIG. 5A, the eye 520 includes an inner corner 560, and outer corner 570, and a pupil portion 580, which may include the iris. In this example, the pupil portion 580 is segmented and includes the iris portion shown in a dashed line. As the right eye moves to the right, the edge of the pupil portion 580 approaches the outer corner 570 of the right eye. The pixel distance 590 is shown to be the distance in pixels between the outer corner 570 of the eye 520 and the edge of the pupil portion 580.

Figure 6:
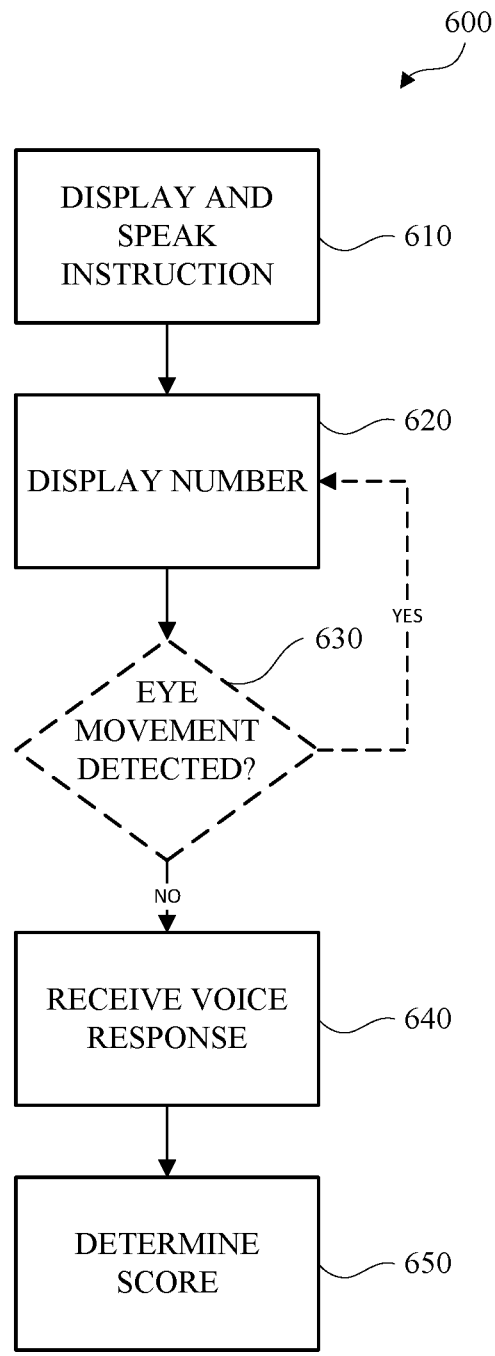
FIG. 6 is a flow diagram of another example of a method 600 for stroke self-detection in accordance with embodiments of this disclosure.

FIG. 6 is a flow diagram of another example of a method 600 for stroke self-detection in accordance with embodiments of this disclosure. The method 600 may be performed by the processor 110 shown in FIGS. 1 and 2. In this example, the method 600 may be performed by the number detection module 230 shown in FIG. 2.

As shown in FIG. 6, the method 600 includes displaying and speaking 610 an instruction. For example, the number detection module 230 may cause the processor 110 to send a signal to the display 115 shown in FIG. 1 to display text of the instruction, send a signal to the one or more speakers 135 shown in FIG. 1 to speak the instruction, or both. In an example for the right hand, the text "Place the phone in your right hand and hold the phone away from your at arm's length. Have the screen facing you." may be displayed on the display 115 and the audible phrase "Place the phone in your right hand and hold the phone away from your at arm's length. Have the screen facing you." may be emitted from the one or more speakers 135. In this example, the text "Keep your head still and look straight ahead. Do not move your eyes." may be displayed on the display 115 and the audible phrase "Keep your head still and look straight ahead. Do not move your eyes." may be emitted from the one or more speakers 135.

The number detection module 230 may cause the processor 110 to send a signal to the display 115 shown in FIG. 1 to display 620 a number. In an example, the number may be displayed as an image or using text. The text "Without moving your eyes, what number do you see?" may be displayed on the display 115 and the audible phrase "Without moving your eyes, what number do you see?" may be emitted from the one or more speakers 135. In some embodiments, the processor 110 may determine 630 whether eye movement is detected. The detection of eye movement may be performed as described in FIG. 4 above.

The method 600 includes receiving 640 a voice response. The voice response may be received by the one or more microphones 145 shown in FIG. 1. The voice response may be processed using any open source speech recognition technique. The voice response may be received as an audible phrase such as, for example, "two," "three," or "four." The one or more microphones 145 may be configured to transmit a signal associated with the voice response to the processor 110. The number detection module 230 may cause the processor 110 to convert the received signal associated with the voice response to text and compare the text to data associated with the displayed number.

The method 600 includes determining 650 a score, for example, a stroke self-detection score. The score may be referred to as a number detection score or a visual perception score. The score may be based on a determination of whether the text associated with the voice response matches the data associated with the displayed number. If the text associated with the voice response matches the data associated with the displayed number, a determination is made that the response was correct, and a score of zero (0) is determined. If the text associated with the voice response does not match the data associated with the displayed number, a determination is made that the response was incorrect, and a score of one (1) is determined. The score may be stored, for example in memory 105 shown in FIG. 1, for later calculation and tabulation.

The method 600 may be repeated while the patient is holding the computing device 100 in their left hand. The displayed and spoken instruction may be adjusted to reflect that the left hand should be used. The displayed number may be changed, for example, the number 2 may be displayed.

Figure 7:
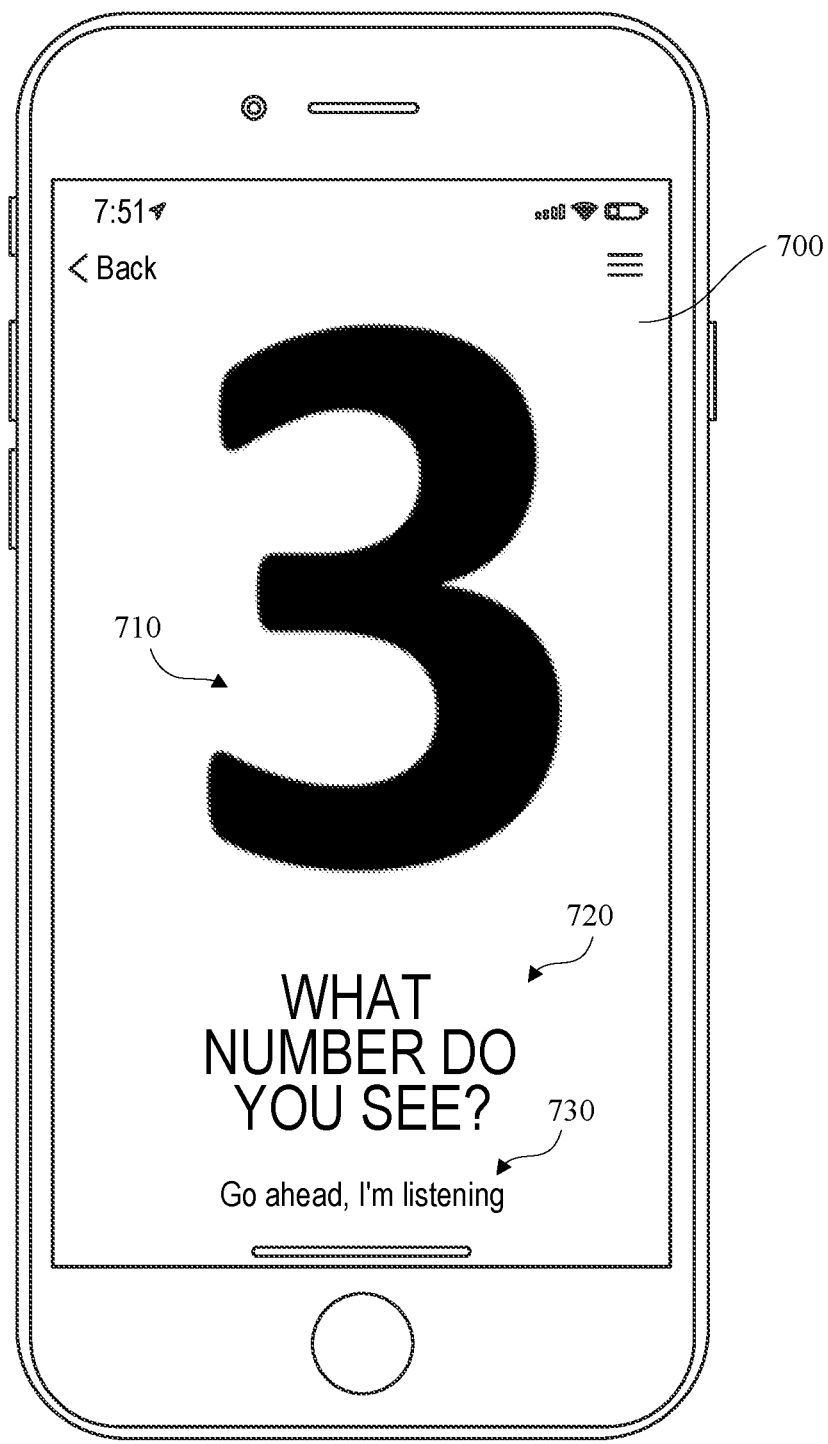
FIG. 7 is a diagram of an example display generated by the number detection module shown in FIG. 2.

FIG. 7 is a diagram of an example display 700 generated by the number detection module 230 shown in FIG. 2. As shown in FIG. 7, a number 710 is displayed. The number 710, in this example, is three (3). In this example, the text instruction 720 is also displayed. Also shown in FIG. 7 is an indication 730 that the one or more microphones 135 are accessible and ready to obtain a voice response.

Figure 8:
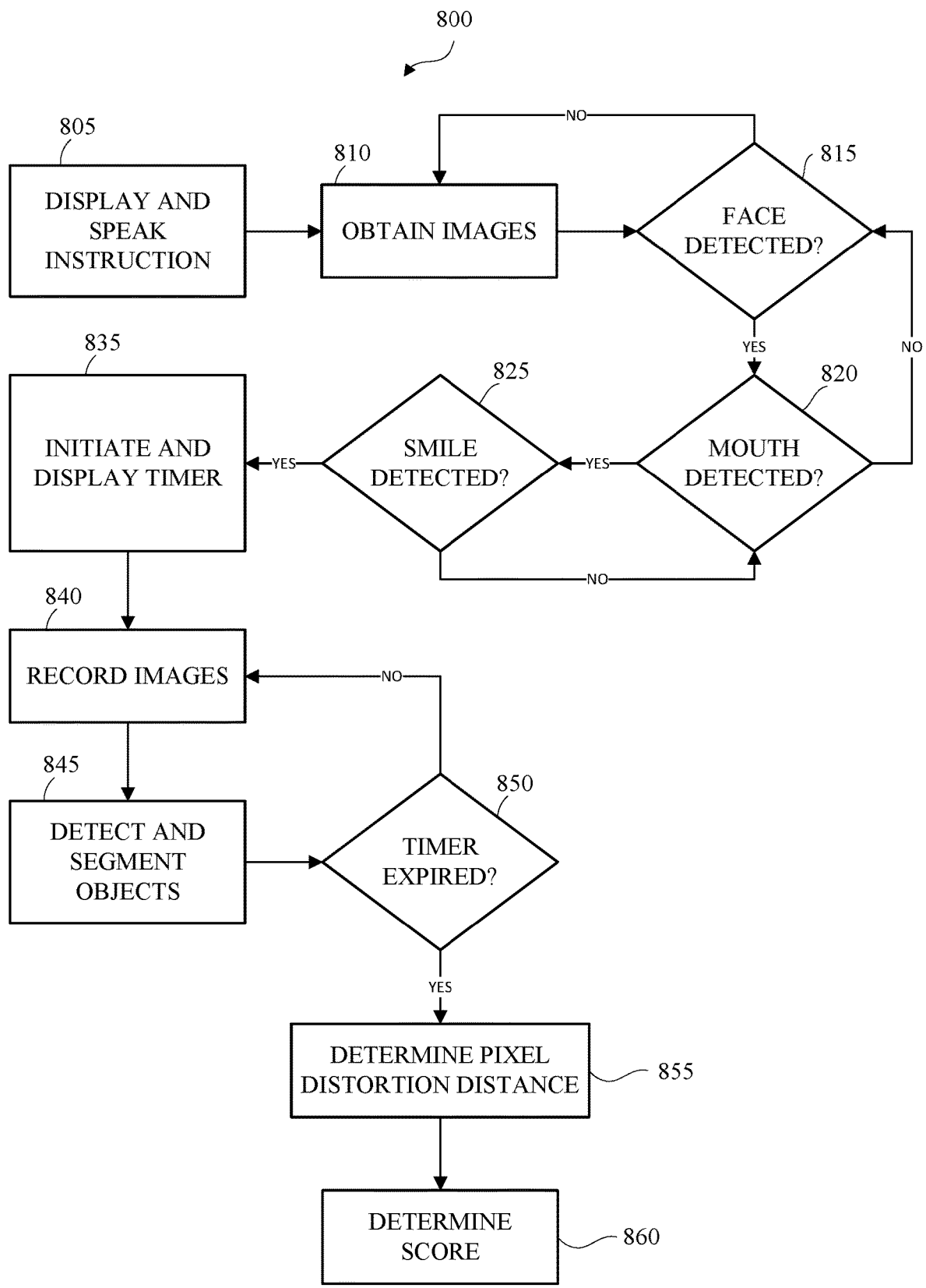
FIG. 8 is a flow diagram of another example of a method for stroke self-detection in accordance with embodiments of this disclosure.

FIG. 8 is a flow diagram of another example of a method 800 for stroke self-detection in accordance with embodiments of this disclosure. The method 800 may be performed by the processor 110 shown in FIGS. 1 and 2. In this example, the method 800 may be performed by the smile detection module 240 shown in FIG. 2.

As shown in FIG. 8, the method 800 includes displaying and speaking 805 an instruction. For example, the smile detection module 240 may cause the processor 110 to send a signal to the display 115 shown in FIG. 1 to display text of the instruction, send a signal to the one or more speakers 135 shown in FIG. 1 to speak the instruction, or both. In an example, the text "Face forward and look directly at the camera. Smile and show your teeth for 3 seconds." may be displayed on the display 115 and the audible phrase "Face forward and look directly at the camera. Smile and show your teeth for 3 seconds." may be emitted from the one or more speakers 135.

The smile detection module 240 may cause the processor 110 to send a signal to the one or more image sensors 140 shown in FIG. 1 to obtain images 810 of the face of the patient. In some implementations, the obtained images may be stored in the memory 105 shown in FIG. 1. The processor 110 may perform face detection 815 on the obtained images. If a face is detected, the processor 110 may perform face landmark detection 820 to determine if a mouth is detected. If a mouth is detected, the processor 110 may determine 825 if a smile is detected. The processor 110 may use ML models for tasks such as classification or object detection. The processor 110 may be configured to track multiple objects, such as a patient's mouth or eyes, or rectangles in the obtained images.

If a smile is detected, the processor 110 may initiate 835 a countdown timer. The countdown timer may be displayed on the display 115 showing the time duration remaining. The countdown timer may be spoken such that it is emitted from the one or more speakers 135.

The smile detection module 240 may cause the processor 110 to send a signal to the one or more image sensors 140 shown in FIG. 1 to record images 840 to obtain a video recording of the face of the patient. In some implementations, the video recording may be stored in the memory 105 shown in FIG. 1.

The processor 110 may obtain images from the video recording and detect and segment 845 objects of the patient's face, for example, eyes, eyebrows, mouth, nose, or any combination thereof. Detecting and segmenting objects of the patient's face may include detecting all detectable two-dimensional (2D) face landmarks and regions, and exposing the face landmarks and regions as properties. The coordinates of the face landmarks may be normalized to the dimensions of a face bounding box, with the origin at the bounding box's lower-left corner. An image point function may be used to convert normalized face landmark points into absolute points within the coordinate system of the image or frame. The processor 110 may perform face detection, face landmark detection, and segmentation using any open source technique.

Once the mouth is segmented and the timer has expired 850, the processor 110 may determine 855 a pixel distortion distance. In an example, the processor 110 may detect a corner of the mouth in one or more frames of the video recording. The video recording may be for any duration. In some examples, the video recording duration may be for 1-3 seconds or more. The corner of the mouth may be determined based on a lip edge. For each frame that the corner of the mouth is detected, the processor 110 calculates 440 an absolute point within the coordinate system of the frame for that corner of the mouth. The processor 110 then compares the absolute points between two frames. The difference between these two points is the pixel distortion distance.

The smile detection module 240 may cause the processor 110 to determine 860 a score, for example, a stroke self-detection score, based on the calculated pixel distortion distance. The score may be referred to as a smile score or a smile detection score. In an example, the processor 110 may determine a score of zero (0) if the pixel distance is less than 2 pixels. If the pixel distance is greater than 2 pixels and less than 5 pixels, the processor may determine a score of one (1). If the pixel distance is greater than 5 pixels and less than 9 pixels, the processor 110 may determine a score of two (2). If the pixel distance is greater than 9 pixels, the processor 110 may determine a score of three (3). The score may be stored, for example in memory 105 shown in FIG. 1, for later calculation and tabulation.

In another example, the processor 110 may determine a total score for smile distortion by determining the position of the corner of the lips in relation to each other. A distortion of less than 0.02 is considered normal and thus the patient receives a score of zero (0). A distortion between 0.02 and 0.05 results in the patient receiving a score of 1. A distortion between 0.05 and 0.09 results in the patient receiving a score of two (2). A distortion greater than 0.09 results in the patient receiving a score of three (3). Similar to the eye movement detection, the software running on the processor 110 detects the patient's mouth and places a bounding box around the mouth. The y data points are recorded, which track where the outermost edges of the lips are in relation to the bounding box surrounding the mouth. The origin (0.0, 0.0) is at the lower-left corner of the bounding box, and the upper-right corner of the box is (1.0, 1.0), similar to an (x, y) coordinate system.

Figure 9:
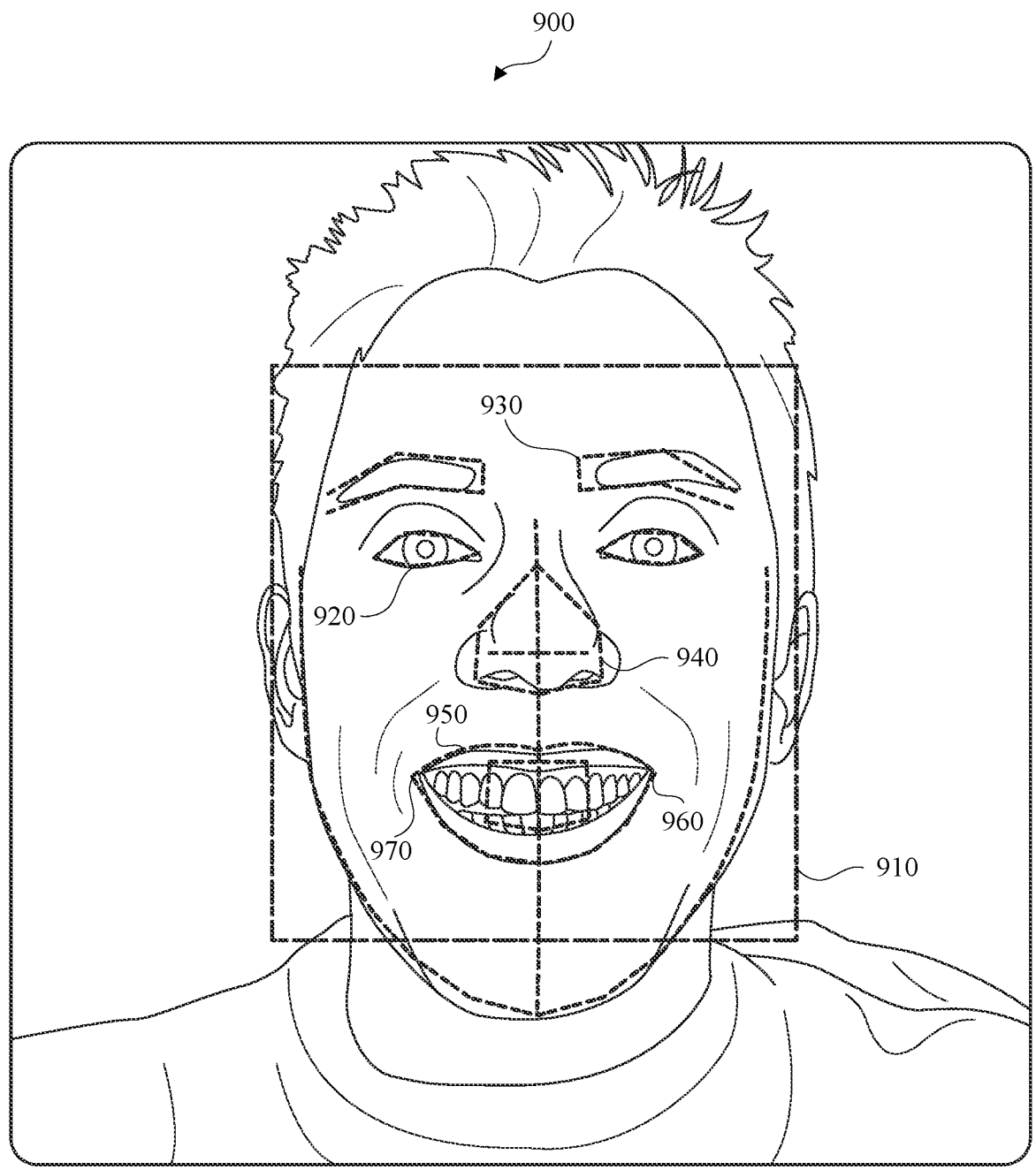
FIG. 9 is a diagram of an example of an image used for smile detection.

FIG. 9 is a diagram of an example of an image 900 used for smile detection. Detecting a smile may include detecting all detectable two-dimensional (2D) face landmarks and regions, and exposing the face landmarks and regions as properties. As shown in FIG. 9, the coordinates of the face landmarks may be normalized to the dimensions of a face bounding box 910, with the origin at the bounding box's lower-left corner. An image point function may be used to convert normalized face landmark points into absolute points within the coordinate system of the image or frame. As shown in FIG. 9, detected objects (shown in bounding boxes as dashed lines) of the patient's face may include, for example, eyes 920, eyebrows 930, nose 940, and mouth 950.

As shown in FIG. 9, the mouth 950 includes a left corner 960 and a right corner 970. The left corner 960, the right corner 970, or both, may be used to determine pixel distortion distance as described in FIG. 8 above.

Figure 10:
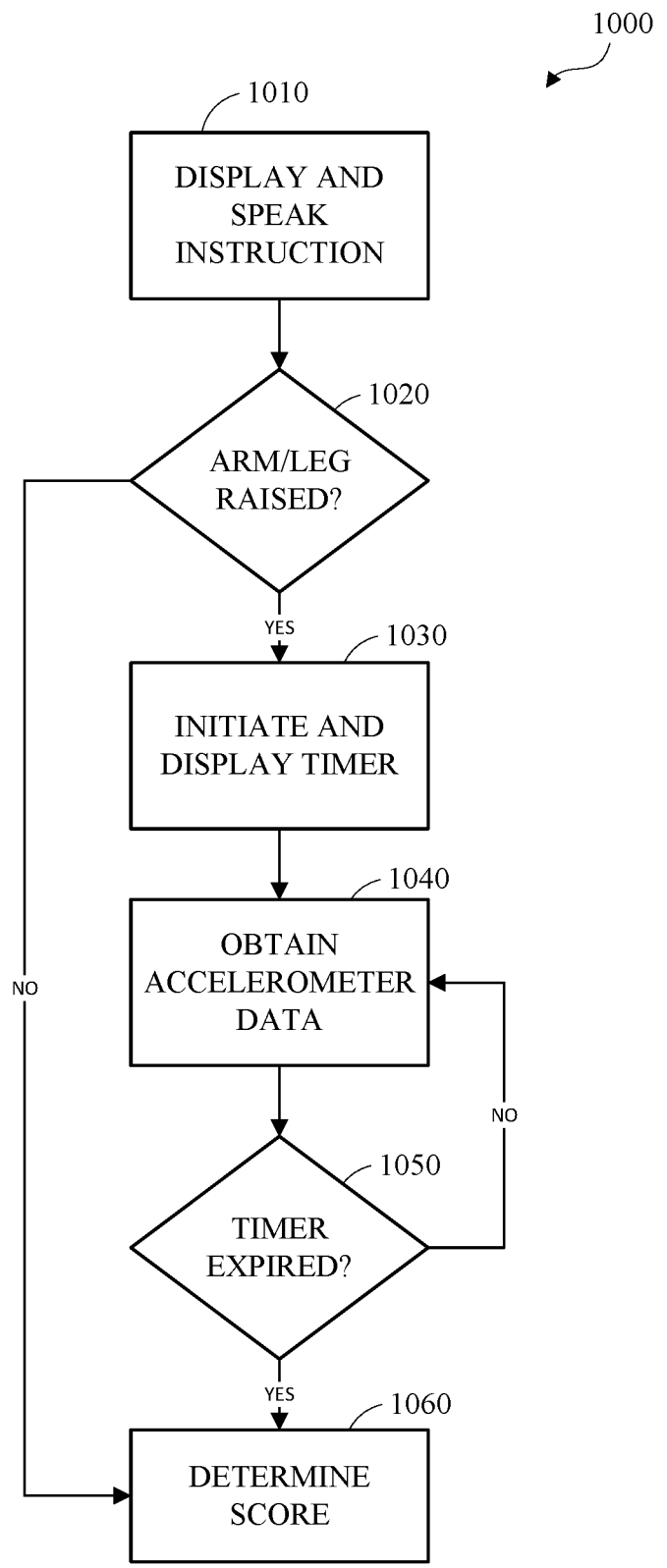
FIG. 10 is a flow diagram of another example of a method for stroke self-detection in accordance with embodiments of this disclosure.

FIG. 10 is a flow diagram of another example of a method 1000 for stroke self-detection in accordance with embodiments of this disclosure. The method 1000 may be performed by the processor 110 shown in FIGS. 1 and 2. In this example, the method 1000 may be performed by the arm motion detection module 250 shown in FIG. 2, the leg motion detection module 260 shown in FIG. 2, or both.

As shown in FIG. 10, the method 1000 includes displaying and speaking 1010 an instruction. The method 1000 may be used to test the right arm of the patient, the left arm of the patient, the right leg of the patient, the left leg of the patient, or any combination thereof. The arm motion detection module 250 or the leg motion detection module 260 may cause the processor 110 to send a signal to the display 115 shown in FIG. 1 to display text of the instruction, send a signal to the one or more speakers 135 shown in FIG. 1 to speak the instruction, or both. In an example for testing motion of the patient's right arm, the text "Place the phone in your right hand. With your right arm outstretched, raise your right arm in the air. Hold your right arm there for 10 seconds." may be displayed on the display 115 and the audible phrase "Place the phone in your right hand. With your right arm outstretched, raise your right arm in the air. Hold your right arm there for 10 seconds." may be emitted from the one or more speakers 135. In an example for testing motion of the patient's right leg, the text "Place your phone in your right hand and hold the phone on your right knee. Raise your right knee in the air. Hold it there for 5 seconds." may be displayed on the display 115 and the audible phrase "Place your phone in your right hand and hold the phone on your right knee. Raise your right knee in the air. Hold it there for 5 seconds." may be emitted from the one or more speakers 135.

The processor 110 may determine 1020 whether the arm or leg is raised based on accelerometer data, image capture data, or both. The accelerometer data is recorded every half second. Each time a motion recording occurs, the total count is incremented by one (1). The processor 110 tracks movement patterns based on the number of counts and the value of the numbers. If the processor 110 determines that the arm or leg is raised, the processor 110 may initiate 1030 a countdown timer. The countdown timer may be displayed on the display 115 showing the time duration remaining. The countdown timer may be spoken such that it is emitted from the one or more speakers 135.

The arm motion detection module 250 or the leg motion detection module 260 may cause the processor to obtain 1040 accelerometer data from the accelerometer 130 shown in FIG. 1. In some embodiments, the processor may also obtain image capture data in this step. Accelerometer data may include acceleration data, vibration data, orientation data, or any combination thereof. The processor 110 is configured to track the motion of the patient's arm or leg based on the accelerometer data, the image capture data, or both. For example, the processor 110 may be configured to determine whether the patient raises their arm or leg, whether the arm or leg drifts downward, whether the arm or leg is raised but not able to remain motionless in the air, whether the arm or leg is able to move at all, or any combination thereof, based on the accelerometer data, the image capture data, or both. The processor 110 may perform motion tracking using any open source motion tracking technique. In some embodiments, the processor 110 may perform motion tracking using machine learning techniques.

The processor 110 may determine 1050 whether the countdown timer has expired. If the countdown timer has expired, the arm motion detection module 250 or the leg motion detection module 260 may cause the processor 110 to determine 1060 a score, for example, a stroke self-detection score, based on the accelerometer data, the image capture data, or both. The score may be referred to as a leg motion score, a leg motion detection score, an arm motion score, an arm motion detection score, a limb motion score, or a limb motion detection score. In an example, if the accelerometer data, the image capture data, or both, indicate that the arm or leg is raised and maintained in the air for the countdown timer duration, the processor 110 may determine a score of zero (0). If accelerometer data, the image capture data, or both, indicate that the arm or the leg drifts downwards before the expiration of the countdown timer, the processor 110 may determine a score of one (1). If the accelerometer data, the image capture data, or both, indicates that the arm or leg is raised but not motionless (i.e., the arm or the leg is shaking) in the air for the duration of the countdown timer, the processor 110 may determine a score of two (2). If the accelerometer data, the image capture data, or both, indicate that the arm or the leg is not raised (i.e., the user is unable to lift the arm or the leg), the processor 110 may determine a score of three (3). If the accelerometer data, the image capture data, or both, indicate that the arm or the leg is motionless (i.e., the user is unable to move the arm or the leg at all), the processor 110 may determine a score of four (4). The method 1000 may be performed for each arm and each leg of the patient, and each limb of the patient may be scored accordingly. The scores may be stored, for example in memory 105 shown in FIG. 1, for later calculation and tabulation.

In another example, for arms, if measurements have less than 22 counts, the patient likely failed the test, i.e., the processor did not record for the full time, meaning that the patient did not complete the test. At shoulder height, the accelerometer data reads 0.0. When the accelerometer data reads between −21.5 and 21.5, the patient has their arm held at an acceptable height for conducting the test. If the accelerometer data reads less than −21.5, the patient is holding their arm too high. If the accelerometer data reads greater than 21.5, the patient is holding their arm too low.

For arms, if 16 or more of the measurements are within the acceptable range, the patient receives a score of zero (0). If 6 to 15 of the measurements are within the acceptable range, the patient receives a score of one (1). If 1 to 5 of the measurements are within the acceptable range, the patient receives a score of two (2). If no measurements are within the acceptable range, the patient receives a score of three (3).

For legs, if the measurements have 12 counts, the patient has successfully completed the test on the first attempt. When the patient's knee is 6 inches above the ground, the adjusted accelerometer data reads 0.0. When the accelerometer data reads between −16.5 and 13.5, the patient has their leg at an acceptable height for conducting the test. If the accelerometer data reads less than −16.5, the patient has their knee lifted too high above the ground. If the accelerometer data reads greater than 13.5, the patient has their knee lifted too low.

For legs, if 7 or more measurements are within the acceptable range, the patient receives a score of zero (0). If 3 to 6 of the measurements are within the acceptable range, the patient receives a score of one (1). If 1 to 2 measurements are within the acceptable range, the patient receives a score of two (2). If no measurements are within the acceptable range, the patient receives a score of three (3).

Figure 11:
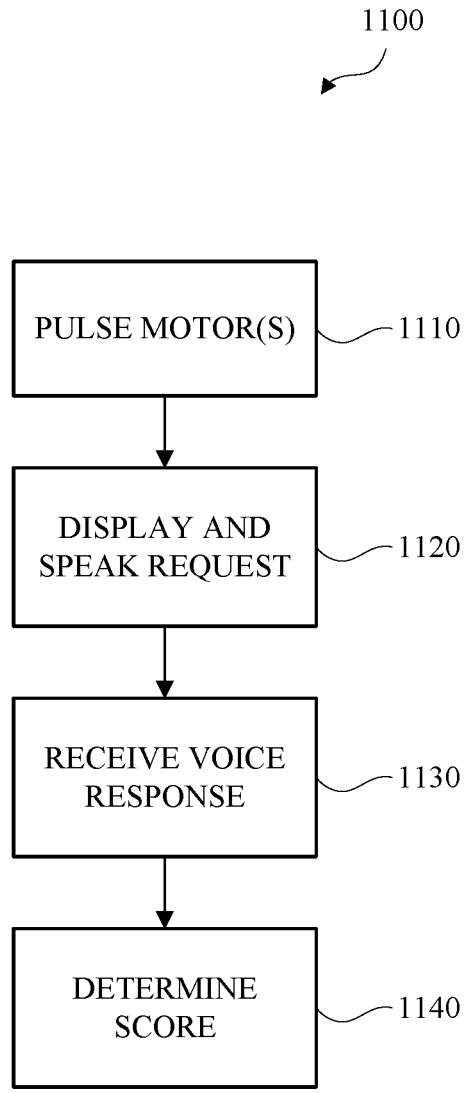
FIG. 11 is a flow diagram of another example of a method for stroke self-detection in accordance with embodiments of this disclosure.

FIG. 11 is a flow diagram of another example of a method 1100 for stroke self-detection in accordance with embodiments of this disclosure. The method 1100 may be performed by the processor 110 shown in FIGS. 1 and 2. In this example, the method 1100 may be performed by the vibration detection module 270 shown in FIG. 2.

As shown in FIG. 11, the vibration detection module 270 may be configured to cause the processor 110 to send a signal to the one or more motors 120 shown in FIG. 1 to pulse 1110 the one or more motors 120. Pulsing the one or more motors 120 will cause the computing device 100 to vibrate. The one or more motors 120 may be pulsed to vibrate the computing device 100 in any vibration pattern, for any duration of time, and for any number of cycles. In an example, the one or more motors 120 may be pulsed such that the computing device 100 vibrates for one second, pauses for one second, and then repeats this vibration pattern two times (i.e., for two additional cycles).

The method 1100 includes displaying and speaking 1120 an instruction. The vibration detection module 270 may cause the processor 110 to send a signal to the display 115 shown in FIG. 1 to display text of the instruction, send a signal to the one or more speakers 135 shown in FIG. 1 to speak the instruction, or both. In an example, the text "Can you feel this vibration?" may be displayed on the display 115 and the audible phrase "Can you feel this vibration?" may be emitted from the one or more speakers 135.

The method 1100 includes receiving 1130 a voice response. The voice response may be received by the one or more microphones 145 shown in FIG. 1. The voice response may be processed using any open source speech recognition technique. The voice response may be received as an audible phrase such as, for example, "yes," "affirmative," "no," or "negative." The one or more microphones 145 may be configured to transmit a signal associated with the voice response to the processor 110. The vibration detection module 230 may cause the processor 110 to convert the received signal associated with the voice response to text and store the text data associated with the voice response.

The method 1100 includes determining 1140 a score, for example, a stroke self-detection score. The score may be referred to as a vibration score or a vibration detection score. The score may be based on a determination of whether the text associated with the voice response matches the data associated with a positive response or a negative response. If the text associated with the voice response matches the data associated with a positive response, a determination is made that the response was correct, and a score of zero (0) is determined. If the text associated with the voice response matches the data associated with a negative response, a determination is made that the response was incorrect, and a score of one (1) is determined. The score may be stored, for example in memory 105 shown in FIG. 1, for later calculation and tabulation.

Figure 12:
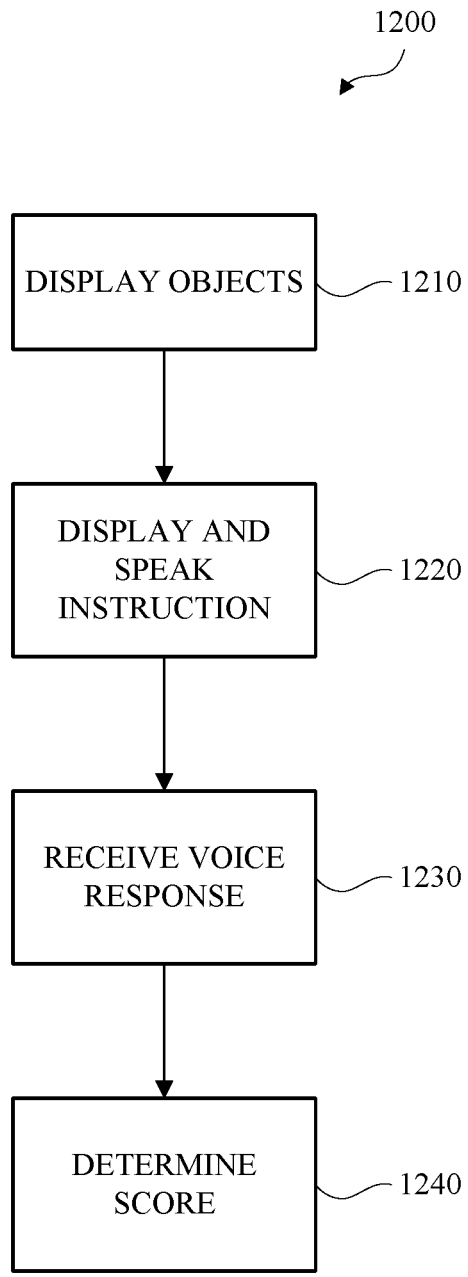
FIG. 12 is a flow diagram of another example of a method for stroke self-detection in accordance with embodiments of this disclosure.

FIG. 12 is a flow diagram of another example of a method 1200 for stroke self-detection in accordance with embodiments of this disclosure. The method 1200 may be performed by the processor 110 shown in FIGS. 1 and 2. In this example, the method 1200 may be performed by the object detection module 280 shown in FIG. 2.

The object detection module 280 may cause the processor 110 to send a signal to the display 115 shown in FIG. 1 to display 1210 one or more objects. The one or more objects may be based on the National Institute of Health (NIH)

stroke scale. For example, the objects may be images of a glove, a key, a cactus, a chair, a hammock, and a feather.

The method 1200 includes displaying and speaking 1220 an instruction. The object detection module 280 may cause the processor 110 to send a signal to the display 115 shown in FIG. 1 to display text of the instruction, send a signal to the one or more speakers 135 shown in FIG. 1 to speak the instruction, or both. The objects may be displayed individually, in one or more groups, or all together. The objects may be displayed with or without the text instruction. In an example, the text "Name these objects." may be displayed along with the objects on the display 115 and the audible phrase "Name these objects." may be emitted from the one or more speakers 135.

The method 1200 includes receiving 1230 a voice response. The voice response may be received by the one or more microphones 145 shown in FIG. 1. The voice response may be processed using any open source speech recognition technique. The voice response may be received as an audible phrase such as, for example, "glove," "key," "hand," or "cactus." The one or more microphones 145 may be configured to transmit a signal associated with the voice response to the processor 110. The object detection module 280 may cause the processor 110 to convert the received signal associated with the voice response to text and compare the text data associated with the voice response to data associated with each displayed object.

The method 1200 includes determining 1240 a score, for example, a stroke self-detection score. The score may be referred to as an object score or an object detection score. The score may be based on a determination of whether the text associated with the voice response matches the data associated with a respective displayed object. If the text associated with the voice response matches the data associated with a respective displayed object, a determination is made that the response was correct. If the text associated with the voice response does not match the data associated with a respective displayed object, a determination is made that the response was incorrect. If the voice responses associated for all six displayed objects are determined to be correct, the processor 110 may determine a score of zero (0). If the voice responses for 3-5 displayed objects are determined to be correct, the processor 110 may determine a score of one (1). If the voice responses for 1-2 displayed objects are determined to be correct, the processor 110 may determine a score of two (2). If the voice responses for all six displayed objects are determined to be incorrect, the processor 110 may determine a score of three (3). The processor 110 may be configured to recognize common mistakes for objects and score them as incorrect, for example if the voice response is "hand" instead of "glove," the voice response will be marked as an incorrect response. The score may be stored, for example in memory 105 shown in FIG. 1, for later calculation and tabulation.

Figure 13:
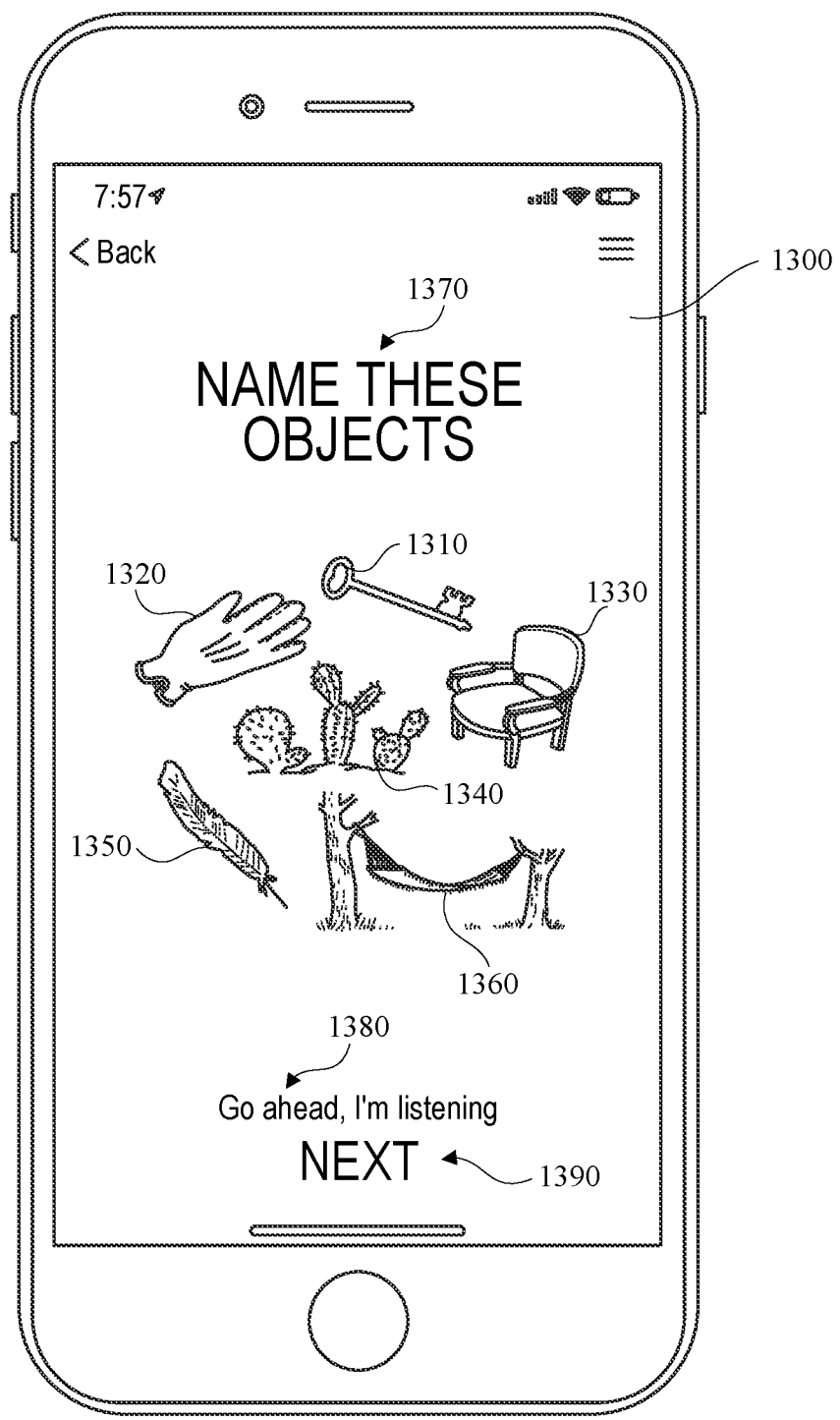
FIG. 13 is a diagram of an example display generated by the object detection module shown in FIG. 2.

FIG. 13 is a diagram of an example display 1300 generated by the object detection module 280 shown in FIG. 2. As shown in FIG. 13, the display 1300 includes images of several objects including a key 1310, a glove 1320, a chair 1330, a cactus 1340, a feather 1350, and a hammock 1360. In this example, the text instruction 1370 is also displayed. Also shown in FIG. 13 is an indication 1380 that the one or more microphones 135 are accessible and ready to obtain a voice response. In this example, the display 1300 may also include an indication 1390 for a user touch or gesture input, such as a button or slider to advance to the next screen.

Figure 14:
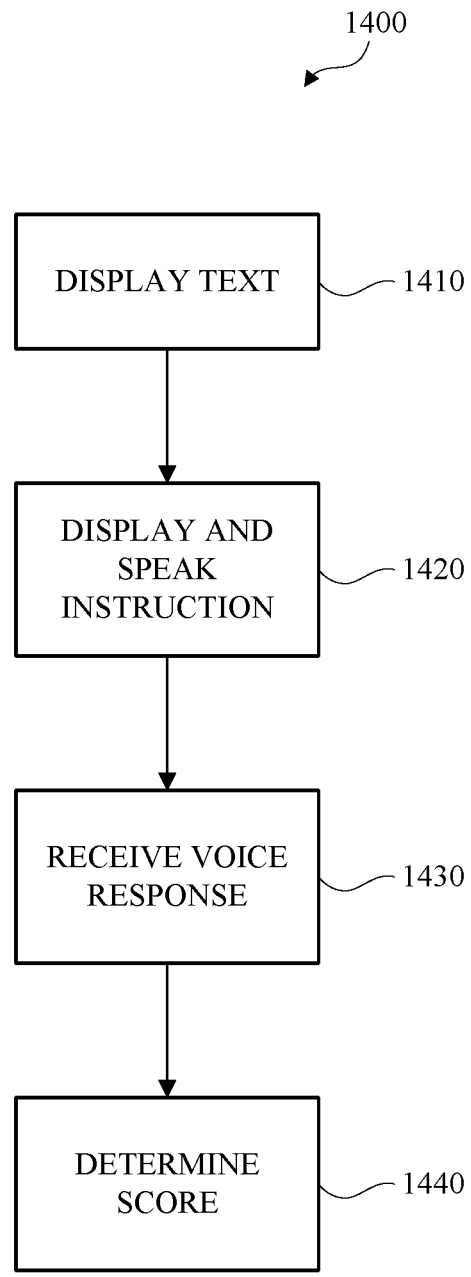
FIG. 14 is a flow diagram of another example of a method for stroke self-detection in accordance with embodiments of this disclosure.

FIG. 14 is a flow diagram of another example of a method 1400 for stroke self-detection in accordance with embodiments of this disclosure. The method 1400 may be performed by the processor 110 shown in FIGS. 1 and 2. In this example, the method 1400 may be performed by the sentence detection module 290 shown in FIG. 2.

The sentence detection module 290 may cause the processor 110 to send a signal to the display 115 shown in FIG. 1 to display 1410 one or more sentences or phrases as text. The one or more sentences or phrases may be based on the National Institute of Health (NIH) stroke scale. For example, the sentences or phrases may include "You know how," "Down to earth," "I got home from work," "Near the table in the dining room," and "They heard him speak on the radio last night."

The method 1400 includes displaying and speaking 1420 an instruction. The sentence detection module 280 may cause the processor 110 to send a signal to the display 115 shown in FIG. 1 to display text of the instruction, send a signal to the one or more speakers 135 shown in FIG. 1 to speak the instruction, or both. The sentences or phrases may be displayed individually, in one or more groups, or all together. The sentences or phrases may be displayed with or without the text instruction. In an example, the text "Read the following sentences." may be displayed along with the sentences or phrases on the display 115 and the audible phrase "Read the following sentences." may be emitted from the one or more speakers 135.

The method 1400 includes receiving 1430 a voice response. The voice response may be received by the one or more microphones 145 shown in FIG. 1. The voice response may be processed using any open source speech recognition technique. The voice response may be received as an audible phrase such as, for example, "Near the table in the dining room" or "Down to earth." The one or more microphones 145 may be configured to transmit a signal associated with the voice response to the processor 110. The sentence detection module 290 may cause the processor 110 to convert the received signal associated with the voice response to text and compare the text data associated with the voice response to data associated with each sentence or phrase.

The method 1400 includes determining 1440 a score, for example, a stroke self-detection score. The score may be referred to as a sentence score or a sentence detection score. The score may be based on a determination of whether the text associated with the voice response matches the data associated with a respective displayed sentence or phrase. The processor 110 is configured to detect whether any words in the voice responses are unclear, slurred, or disorganized (e.g., incorrect words, words in incorrect order, gaps of greater than three seconds between words). If the text associated with the voice response matches the data associated with a respective displayed sentence or phrase, a determination is made that the response was correct. If the text associated with the voice response does not match the data associated with a respective displayed sentence or phrase (i.e., one or more words does not match), a determination is made that the response was incorrect. If the voice responses associated with all the displayed sentences or phrases are determined to be correct, the processor 110 may determine a score of zero (0). If any words in the voice responses are unclear, slurred, or disorganized, the processor 110 may determine a score of one (1). If the voice responses for all the displayed sentences or phrases are determined to be incorrect, the processor 110 may determine a score of two (2). The score may be stored, for example in memory 105 shown in FIG. 1, for later calculation and tabulation.

Figure 15:
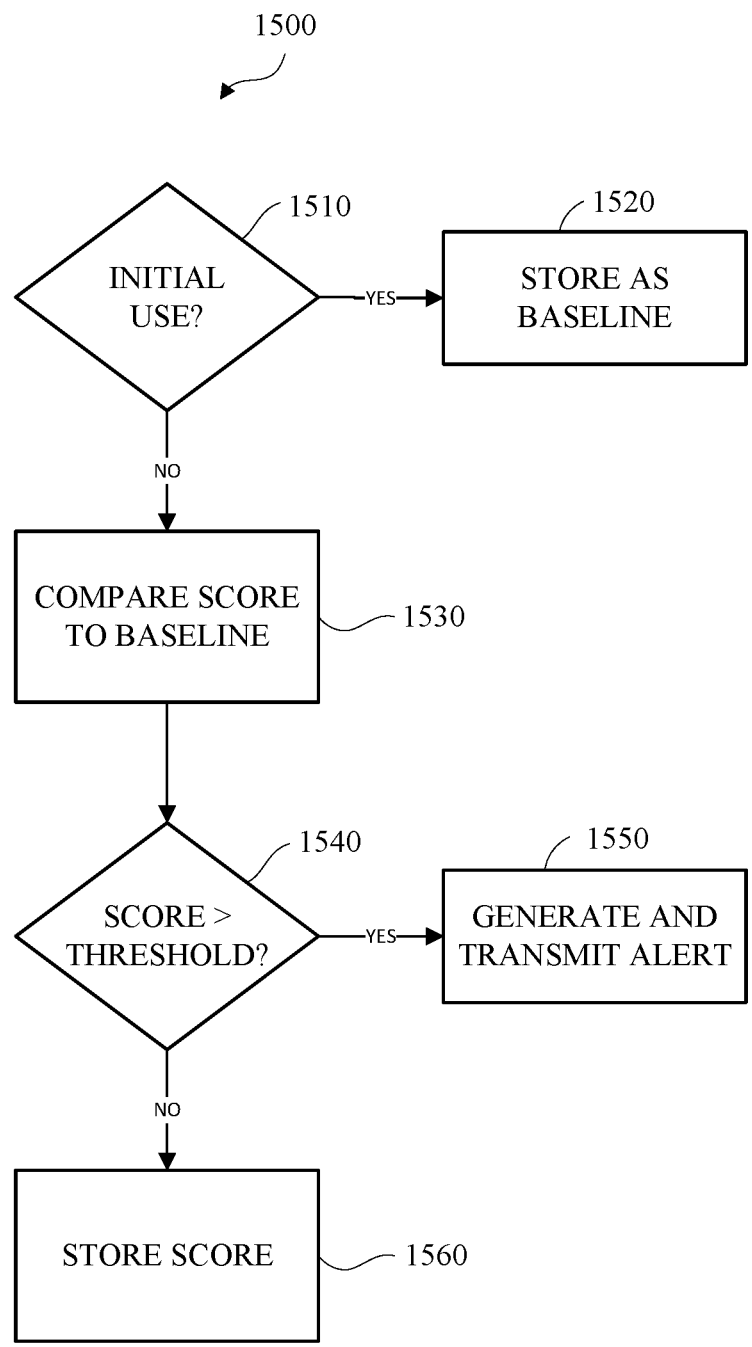
FIG. 15 is a flow diagram of an example scoring method that may be used by any of the embodiments disclosed herein.

FIG. 15 is a flow diagram of an example scoring method 1500 that may be used by any of the embodiments disclosed herein. As shown in FIG. 15, the method 1500 includes determining whether the current use of the method is an initial use. The initial use may be more than one use, for example, the initial use may include the first 3 to 10 uses of the method. If it is determined that the current use is the initial use or fits the criteria of an initial use, the determined score is stored 1520 as a baseline. The baseline may be an average of two or more determined scores. If it is determined that the current use is not the initial use or does not fit the criteria of an initial use, the method 1500 includes comparing the determined score to the baseline.

The method 1500 includes determining 1540 whether the difference in score relative to the baseline is greater than a threshold. If the difference in score relative to the baseline is above a threshold, the method includes generating and transmitting 1550 an alert that indicates that the patient may be experiencing a stroke. The alert may be transmitted to the patient's primary care physician, emergency contact, emergency medical services, telemedicine provider, or any combination thereof. In some embodiments, the method 1500 may include requesting permission from the patient to transmit the alert. If the difference in score relative to the baseline is below the threshold, the method includes storing 1560 the score. In some embodiments, the scores from one or more methods may be tabulated and displayed numerically and qualitatively on the display 115.

One or more methods described herein may be combined, and the scores may be summed to determine an overall score. The overall score may be used to determine whether to contact the patient's primary care physician, emergency contact, emergency medical services, telemedicine provider, or any combination thereof. The scores may be tabulated and displayed numerically and qualitatively on the display.

Although some embodiments herein refer to methods, it will be appreciated by one skilled in the art that they may also be embodied as a system or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "processor," "device," or "system." Furthermore, aspects of the present invention may take the form of a computer program product embodied in one or more computer readable mediums having computer readable program code embodied thereon. Any combination of one or more computer readable mediums may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to CDs, DVDs, wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks. The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks. The flowcharts and block diagrams in the figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

While the disclosure has been described in connection with certain embodiments, it is to be understood that the disclosure is not to be limited to the disclosed embodiments but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. A computing device for stroke self-detection, the computing device comprising:
    a display configured to display an instruction;
    a plurality of sensors that include an accelerometer, a camera, and a microphone;
    a memory; and
    a processor configured to:
        obtain sensor data based on the instruction, wherein the sensor data includes accelerometer data from the accelerometer, image capture data from the camera, and microphone data from the microphone that includes voice data associated with a patient response;
        convert the voice data to text data;
        determine a stroke self-detection score based on the obtained sensor data, wherein the determination of the stroke self-detection score includes a comparison of the text data to data associated with the instruction and a determination of a cognitive score, wherein the instruction includes a request for patient age, and wherein the determination of the cognitive score comprises:
            a determination that the cognitive score is zero (0) on a condition that the text data matches the data associated with the instruction; and
            a determination that the cognitive score is one (1) on a condition that the text data does not match the data associated with the instruction;
        store the stroke self-detection score in the memory;
        display the stroke self-detection score on the display as a result summary; and
        on a condition that the stroke self-detection score is above a threshold, transmit an alert.

2. The computing device of claim 1, further comprising a speaker, wherein the processor is further configured to:
    convert the instruction to speech data; and
    emit the speech data as a voice instruction via the speaker.

3. The computing device of claim 1, wherein the determination of the stroke self-detection score includes a determination of a cognitive score, wherein the instruction includes a request for a current month, and wherein the determination of the cognitive score comprises:
    a determination that the cognitive score is zero (0) on a condition that the text data matches the data associated with the instruction; and
    a determination that the cognitive score is one (1) on a condition that the text data does not match the data associated with the instruction.

4. The computing device of claim 1, wherein the determination of the stroke self-detection score includes a determination of a number detection score, wherein the instruction includes an image of an object, and wherein the determination of the number detection score comprises:
    a determination that the number detection score is zero (0) on a condition that the text data matches the data associated with the instruction; and
    a determination that the number detection score is one (1) on a condition that the text data does not match the data associated with the instruction.

5. The computing device of claim 1, further comprising a motor configured to pulse, wherein the determination of the stroke self-detection score includes a determination of a vibration score, wherein the instruction includes a request for a response associated with a vibration caused by the motor, and wherein the determination of the vibration score comprises:
    a determination that the vibration score is zero (0) on a condition that the text data matches data associated with a positive response; and
    a determination that the vibration score is one (1) on a condition that the text data matches data associated with a negative response.

6. The computing device of claim 1, wherein the determination of the stroke self-detection score includes a determination of an object detection score, wherein the instruction includes an image of a plurality of objects, and wherein the determination of the object detection score comprises:
    a determination that the object detection score is zero (0) on a condition that the text data matches data associated with each of the plurality of objects;
    a determination that the object detection score is two (2) on a condition that the text data matches data associated with at least one of the plurality of objects;
    a determination that the object detection score is one (1) on a condition that the text data matches data associated with at least three of the plurality of objects; and
    a determination that the object detection score is three (3) on a condition that the text data does not match data associated with any of the plurality of objects.

7. The computing device of claim 1, wherein the determination of the stroke self-detection score includes a determination of a sentence detection score, wherein the instruction includes a plurality of sentences, and wherein the determination of the sentence detection score comprises:
    a determination that the sentence detection score is zero (0) on a condition that the text data matches data associated with each of the plurality of sentences;
    a determination that the sentence detection score is one (1) on a condition that the text data does not match data associated with at least one of the plurality of sentences; and a determination that the sentence detection score is two (2) on a condition that the text data does not match data associated with any of the plurality of sentences.

8. The computing device of claim 1, wherein the image capture data includes a frame that includes a face, the processor further configured to:
perform face detection to identify an eye on the face;
detect a pupil position of the eye on the frame;
calculate a relative pupil position within a bounding box surrounding the eye.

9. The computing device of claim 8, wherein the determination of the stroke self-detection score includes a determination of an eye movement score based on a right eye passing score of 0.1 and a left eye passing score of 0.07, wherein the determination of the eye movement score comprises:
a determination that the eye movement score is zero (0) on a condition that the right eye passing score and the left eye passing score are met;
a determination that the eye movement score is one (1) on a condition that a left eye distance is greater than the left eye passing score or a right eye distance is greater than the right eye passing score;
a determination that the eye movement score is two (2) on a condition that the left eye distance is greater than the left eye passing score and the right eye distance is greater than the right eye passing score; and
a determination that the eye movement score is two (2) on a condition that one eye receives a passing score and the other eye receives a failing score.

10. The computing device of claim 1, wherein the image capture data includes a first frame that includes a face and a second frame that includes the face, the processor further configured to:
perform face detection to identify a mouth on the face, wherein the mouth has a left corner and a right corner;
detect a smile based on the right corner or the left corner;
calculate a first absolute point on the first frame, wherein the first absolute point is based on the right corner or the left corner;
calculate a second absolute point on the second frame, wherein the second absolute point is based on a same corner as the first absolute point; and
calculate a pixel distortion value, wherein the pixel distortion value is based on a difference of a measurement between the first absolute point and the second absolute point.

11. The computing device of claim 10, wherein the determination of the stroke self-detection score includes a determination of a smile detection score, wherein the determination of the smile detection score comprises:
a determination that the smile detection score is zero (0) on a condition that the pixel distortion value is less than 0.02;
a determination that the smile detection score is one (1) on a condition that the pixel distortion value is between 0.02 and 0.05;
a determination that the smile detection score is two (2) on a condition that the pixel distortion value is between 0.05 and 0.09; and
a determination that the smile detection score is three (3) on a condition that the pixel distortion value is greater than 0.09.

12. The computing device of claim 1, wherein the determination of the stroke self-detection score includes a determination of an arm motion detection score, wherein the determination of the arm motion detection score comprises:
a determination that the arm motion detection score is zero (0) on a condition that the accelerometer data indicates that an arm is maintained in an elevated position for a predetermined duration;
a determination that the arm motion detection score is one (1) on a condition that the accelerometer data indicates that the arm drifted downward prior to an expiration of the predetermined duration;
a determination that the arm motion detection score is two (2) on a condition that the accelerometer data indicates that the arm is elevated and shaking;
a determination that the arm motion detection score is three (3) on a condition that the accelerometer data indicates that the arm is not elevated; and
a determination that the arm motion detection score is four (4) on a condition that the accelerometer data indicates that the arm is motionless.

13. The computing device of claim 1, wherein the determination of the stroke self-detection score includes a determination of a leg motion detection score, wherein the determination of the leg motion detection score comprises:
a determination that the leg motion detection score is zero (0) on a condition that the accelerometer data indicates that a leg is maintained in an elevated position for a predetermined duration;
a determination that the leg motion detection score is one (1) on a condition that the accelerometer data indicates that the leg drifted downward prior to an expiration of the predetermined duration;
a determination that the leg motion detection score is two (2) on a condition that the accelerometer data indicates that the leg is elevated and shaking;
a determination that the leg motion detection score is three (3) on a condition that the accelerometer data indicates that the leg is not elevated; and
a determination that the leg motion detection score is four (4) on a condition that the accelerometer data indicates that the leg is motionless.

14. A computing device for stroke self-detection, the computing device comprising:
a display configured to display an instruction;
a microphone;
a memory; and
a processor configured to:
obtain microphone data from the microphone, wherein the microphone data includes voice data associated with a patient response;
convert the voice data to text data;
determine a stroke self-detection score based on a comparison of the text data to data associated with the instruction and a determination of a cognitive score, wherein the instruction includes a request for a current month, and wherein the determination of the cognitive score comprises:
a determination that the cognitive score is zero (0) on a condition that the text data matches the data associated with the instruction; and
a determination that the cognitive score is one (1) on a condition that the text data does not match the data associated with the instruction;
store the stroke self-detection score in the memory;
display the stroke self-detection score on the display as a result summary; and
on a condition that the stroke self-detection score is above a threshold, transmit an alert.

15. The computing device of claim 14, wherein the determination of the stroke self-detection score includes a determination of a number detection score, wherein the instruction includes an image of a number, and wherein the determination of the number detection score comprises:
- a determination that the number detection score is zero (0) on a condition that the text data matches the data associated with the instruction; and
- a determination that the number detection score is one (1) on a condition that the text data does not match the data associated with the instruction.

16. The computing device of claim 14, further comprising a motor, wherein the determination of the stroke self-detection score includes a determination of a vibration score, wherein the instruction includes a request for a response associated with a vibration caused by the motor, and wherein the determination of the vibration score comprises:
- a determination that the vibration score is zero (0) on a condition that the text data matches data associated with a positive response; and
- a determination that the vibration score is one (1) on a condition that the text data matches data associated with a negative response.

17. The computing device of claim 14, wherein the determination of the stroke self-detection score includes a determination of an object detection score, wherein the instruction includes an image of a plurality of objects, and wherein the determination of the object detection score comprises:
- a determination that the object detection score is zero (0) on a condition that the text data matches data associated with each of the plurality of objects;
- a determination that the object detection score is two (2) on a condition that the text data matches data associated with at least one of the plurality of objects;
- a determination that the object detection score is one (1) on a condition that the text data matches data associated with at least three of the plurality of objects; and
- a determination that the object detection score is three (3) on a condition that the text data does not match data associated with any of the plurality of objects.

\* \* \* \* \*